US010123797B2

(12) United States Patent
Katre et al.

(10) Patent No.: US 10,123,797 B2
(45) Date of Patent: *Nov. 13, 2018

(54) SURGICAL FASTENER APPLYING APPARATUS

(71) Applicant: Covidien LP, Mansfield, MA (US)

(72) Inventors: Nikhil R. Katre, Maharashtra (IN);
Cinish P. Varghese, Adimaly (IN);
Arvind Kumar Gupta, Uttar Pradesh (IN); Salman Kapadia, Madhya Pradesh (IN); Sandeep H. Ambardekar, Mumbai (IN)

(73) Assignee: Covidien LP, Mansfield, MA (US)

( * ) Notice: Subject to any disclaimer, the term of this patent is extended or adjusted under 35 U.S.C. 154(b) by 567 days.

This patent is subject to a terminal disclaimer.

(21) Appl. No.: 14/809,552

(22) Filed: Jul. 27, 2015

(65) Prior Publication Data

US 2015/0327855 A1    Nov. 19, 2015

Related U.S. Application Data

(63) Continuation of application No. 13/546,976, filed as application No. PCT/US2012/049347 on Aug. 2, 2012, now Pat. No. 9,155,537.

(Continued)

(51) Int. Cl.
*A61B 17/068*    (2006.01)
*A61B 17/072*    (2006.01)
(Continued)

(52) U.S. Cl.
CPC ........ *A61B 17/072* (2013.01); *A61B 17/0686* (2013.01); *A61B 17/07207* (2013.01);
(Continued)

(58) Field of Classification Search
CPC . A61B 17/068; A61B 17/0686; A61B 17/072; A61B 17/07207; A61B 17/115;
(Continued)

(56) References Cited

U.S. PATENT DOCUMENTS 3,079,606 A    3/1963    Bobrov et al.
3,490,675 A    1/1970    Green et al.
(Continued)

FOREIGN PATENT DOCUMENTS

AU    198654765    9/1986
DE    2744824 A1    4/1978
(Continued)

OTHER PUBLICATIONS

International Search Report dated Jan. 10, 2013 for copending International Application No. PCT/US2012/049347.

(Continued)

*Primary Examiner* — Scott A. Smith

(57) ABSTRACT

A surgical fastener applying apparatus for applying fasteners to body tissue. The apparatus includes a cartridge receiving half-section defining an elongated channel member configured to releasably receive a stationary housing of a firing assembly. The stationary housing is dimensioned to releasably receive a single use loading unit therein, and includes a lockout structure that prevents insertion of the single use loading unit into the stationary housing after the stationary housing is mounted to the cartridge receiving half-section.

9 Claims, 29 Drawing Sheets

Related U.S. Application Data

(60) Provisional application No. 61/521,074, filed on Aug. 8, 2011.

(51) Int. Cl.
  *A61B 17/115* (2006.01)
  *A61B 17/29* (2006.01)

(52) U.S. Cl.
  CPC ... *A61B 17/115* (2013.01); *A61B 2017/07214* (2013.01); *A61B 2017/07278* (2013.01); *A61B 2017/2946* (2013.01)

(58) Field of Classification Search
  CPC A61B 2017/07214; A61B 2017/07278; A61B 2017/2946
  USPC .............. 227/19, 176.1, 175.2, 175.3, 180.1; 606/139, 219
  See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,550,870 A | 11/1985 | Krumme et al. |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |

(56) References Cited

U.S. PATENT DOCUMENTS

| | | |
|---|---|---|
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |

(56) References Cited

U.S. PATENT DOCUMENTS

| | | |
|---|---|---|
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |

(56) References Cited

U.S. PATENT DOCUMENTS

| | | |
|---|---|---|
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,784,663 B2 | 8/2010 | Shelton, IV |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |

(56) References Cited

U.S. PATENT DOCUMENTS

| | | |
|---|---|---|
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,267,300 B2 | 9/2012 | Boudreaux |
| 8,272,554 B2 | 9/2012 | Whitman et al. |
| 8,397,972 B2* | 3/2013 | Kostrzewski .... A61B 17/07207 227/175.2 |
| 8,636,766 B2* | 1/2014 | Milliman ......... A61B 17/07207 227/175.2 |
| 9,155,537 B2 | 10/2015 | Katre et al. |
| 9,271,728 B2* | 3/2016 | Gupta ............. A61B 17/07207 |
| 9,289,211 B2* | 3/2016 | Williams ......... A61B 17/07207 |
| 9,451,959 B2* | 9/2016 | Patankar ......... A61B 17/07207 |

(56) References Cited

U.S. PATENT DOCUMENTS

| | | | |
|---|---|---|---|
| 9,539,007 B2* | 1/2017 | Dhakad | A61B 17/07207 |
| 9,724,095 B2* | 8/2017 | Gupta | A61B 17/07207 |
| 9,757,126 B2* | 9/2017 | Cappola | A61B 17/072 |
| 2004/0108357 A1 | 6/2004 | Milliman et al. | |
| 2004/0199180 A1 | 10/2004 | Knodel et al. | |
| 2004/0199181 A1 | 10/2004 | Knodel et al. | |
| 2004/0232201 A1 | 11/2004 | Wenchell et al. | |
| 2004/0243151 A1 | 12/2004 | Demmy et al. | |
| 2004/0267310 A1 | 12/2004 | Racenet et al. | |
| 2005/0023324 A1 | 2/2005 | Doll et al. | |
| 2005/0103819 A1 | 5/2005 | Racenet et al. | |
| 2005/0119669 A1 | 6/2005 | Demmy | |
| 2005/0189397 A1 | 9/2005 | Jankowski | |
| 2005/0216055 A1 | 9/2005 | Scirica et al. | |
| 2005/0263562 A1 | 12/2005 | Shelton et al. | |
| 2006/0049229 A1 | 3/2006 | Milliman et al. | |
| 2006/0081678 A1 | 4/2006 | Ehrenfels et al. | |
| 2006/0180634 A1 | 8/2006 | Shelton et al. | |
| 2006/0289602 A1 | 12/2006 | Wales et al. | |
| 2007/0027469 A1 | 2/2007 | Smith et al. | |
| 2007/0073341 A1 | 3/2007 | Smith et al. | |
| 2007/0084897 A1 | 4/2007 | Shelton et al. | |
| 2007/0084899 A1 | 4/2007 | Taylor | |
| 2007/0102472 A1 | 5/2007 | Shelton | |
| 2007/0106317 A1 | 5/2007 | Shelton et al. | |
| 2007/0119901 A1 | 5/2007 | Ehrenfels et al. | |
| 2007/0145096 A1 | 6/2007 | Viola et al. | |
| 2007/0170225 A1 | 7/2007 | Shelton et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0179528 A1 | 8/2007 | Soltz et al. | |
| 2007/0194079 A1 | 8/2007 | Hueil et al. | |
| 2007/0194081 A1 | 8/2007 | Hueil et al. | |
| 2007/0194082 A1 | 8/2007 | Morgan et al. | |
| 2007/0221700 A1 | 9/2007 | Ortiz et al. | |
| 2007/0295780 A1 | 12/2007 | Shelton et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0078800 A1 | 4/2008 | Hess et al. | |
| 2008/0078802 A1 | 4/2008 | Hess et al. | |
| 2008/0078803 A1 | 4/2008 | Shelton et al. | |
| 2008/0078804 A1 | 4/2008 | Shelton et al. | |
| 2008/0078806 A1 | 4/2008 | Omaits et al. | |
| 2008/0078808 A1 | 4/2008 | Hess et al. | |
| 2008/0110961 A1 | 5/2008 | Voegele et al. | |
| 2008/0149685 A1 | 6/2008 | Smith et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0287987 A1 | 11/2008 | Boyden et al. | |
| 2008/0296344 A1 | 12/2008 | Cropper et al. | |
| 2008/0296346 A1 | 12/2008 | Shelton, IV et al. | |
| 2008/0308602 A1 | 12/2008 | Timm et al. | |
| 2008/0308603 A1 | 12/2008 | Shelton et al. | |
| 2009/0001121 A1 | 1/2009 | Hess et al. | |
| 2009/0001124 A1 | 1/2009 | Hess et al. | |
| 2009/0001130 A1 | 1/2009 | Hess et al. | |
| 2009/0005808 A1 | 1/2009 | Hess et al. | |
| 2009/0065549 A1 | 3/2009 | Viola | |
| 2009/0078739 A1 | 3/2009 | Viola | |
| 2009/0090763 A1 | 4/2009 | Zemlok et al. | |
| 2009/0090766 A1 | 4/2009 | Knodel | |
| 2009/0209946 A1 | 8/2009 | Swayze et al. | |
| 2009/0209990 A1 | 8/2009 | Yates et al. | |
| 2009/0236395 A1 | 9/2009 | Scirica | |
| 2009/0242610 A1 | 10/2009 | Shelton, IV et al. | |
| 2009/0255974 A1 | 10/2009 | Viola | |
| 2009/0272787 A1 | 11/2009 | Scirica | |
| 2009/0277946 A1 | 11/2009 | Marczyk | |
| 2009/0277949 A1 | 11/2009 | Viola et al. | |
| 2009/0283568 A1 | 11/2009 | Racenet et al. | |
| 2009/0306708 A1 | 12/2009 | Shah | |
| 2009/0308907 A1 | 12/2009 | Nalagatla et al. | |
| 2010/0012703 A1 | 1/2010 | Calabrese et al. | |
| 2010/0012704 A1 | 1/2010 | Tarinelli Racenet et al. | |
| 2010/0069942 A1 | 3/2010 | Shelton, IV | |
| 2010/0072251 A1 | 3/2010 | Baxter, III et al. | |
| 2010/0072254 A1 | 3/2010 | Aranyi et al. | |
| 2010/0076429 A1 | 3/2010 | Heinrich | |
| 2010/0076459 A1 | 3/2010 | Farascioni | |
| 2010/0089970 A1 | 4/2010 | Smith et al. | |
| 2010/0127041 A1 | 5/2010 | Morgan et al. | |
| 2010/0127042 A1 | 5/2010 | Shelton, IV | |
| 2010/0133317 A1 | 6/2010 | Shelton, IV et al. | |
| 2010/0133318 A1 | 6/2010 | Boudreaux | |
| 2010/0147921 A1 | 6/2010 | Olson | |
| 2010/0147922 A1 | 6/2010 | Olson | |
| 2010/0155453 A1 | 6/2010 | Bombard et al. | |
| 2010/0170931 A1 | 7/2010 | Viola | |
| 2010/0193566 A1 | 8/2010 | Scheib et al. | |
| 2010/0213241 A1 | 8/2010 | Bedi | |
| 2010/0224668 A1 | 9/2010 | Fontayne et al. | |
| 2010/0230468 A1 | 9/2010 | Viola | |
| 2010/0237130 A1 | 9/2010 | Scirica | |
| 2010/0243709 A1 | 9/2010 | Hess et al. | |
| 2010/0249802 A1 | 9/2010 | May et al. | |
| 2010/0252611 A1 | 10/2010 | Ezzat et al. | |
| 2010/0252612 A1 | 10/2010 | Viola | |
| 2010/0264192 A1 | 10/2010 | Marczyk | |
| 2010/0264193 A1 | 10/2010 | Huang et al. | |
| 2010/0264194 A1 | 10/2010 | Huang et al. | |
| 2010/0294828 A1 | 11/2010 | Bindra et al. | |
| 2010/0294829 A1 | 11/2010 | Giordano et al. | |
| 2010/0301095 A1 | 12/2010 | Shelton, IV et al. | |
| 2010/0305552 A1 | 12/2010 | Shelton, IV et al. | |
| 2010/0308100 A1 | 12/2010 | Boudreaux | |
| 2010/0320252 A1 | 12/2010 | Viola et al. | |
| 2010/0320254 A1 | 12/2010 | Zemlok et al. | |
| 2011/0006099 A1 | 1/2011 | Hall et al. | |
| 2011/0006101 A1 | 1/2011 | Hall et al. | |
| 2011/0006103 A1 | 1/2011 | Laurent et al. | |
| 2011/0011914 A1 | 1/2011 | Baxter, III et al. | |
| 2011/0011915 A1 | 1/2011 | Shelton, IV | |
| 2011/0017801 A1 | 1/2011 | Zemlok et al. | |
| 2011/0024477 A1 | 2/2011 | Hall | |
| 2011/0024478 A1 | 2/2011 | Shelton, IV | |
| 2011/0036887 A1 | 2/2011 | Zemlok et al. | |
| 2011/0036888 A1 | 2/2011 | Pribanic et al. | |
| 2011/0036890 A1 | 2/2011 | Ma | |
| 2011/0036891 A1 | 2/2011 | Zemlok et al. | |
| 2011/0036892 A1 | 2/2011 | Marczyk et al. | |
| 2011/0036895 A1 | 2/2011 | Marczyk et al. | |
| 2011/0042439 A1 | 2/2011 | Johnson et al. | |
| 2011/0042441 A1 | 2/2011 | Shelton, IV et al. | |
| 2011/0062213 A1 | 3/2011 | Scirica et al. | |
| 2011/0068145 A1 | 3/2011 | Bedi et al. | |
| 2011/0068148 A1 | 3/2011 | Hall et al. | |
| 2011/0084114 A1 | 4/2011 | Marczyk et al. | |
| 2011/0084115 A1 | 4/2011 | Bedi et al. | |
| 2011/0087276 A1 | 4/2011 | Bedi et al. | |
| 2011/0089221 A1 | 4/2011 | Masiakos et al. | |
| 2011/0095067 A1 | 4/2011 | Ohdaira | |
| 2011/0101067 A1 | 5/2011 | Johnson et al. | |
| 2011/0101069 A1 | 5/2011 | Bombard et al. | |
| 2011/0108603 A1 | 5/2011 | Racenet et al. | |
| 2011/0114702 A1 | 5/2011 | Farascioni | |
| 2011/0121049 A1 | 5/2011 | Malinouskas et al. | |
| 2011/0132961 A1 | 6/2011 | Whitman et al. | |
| 2011/0132963 A1 | 6/2011 | Giordano et al. | |
| 2011/0132964 A1 | 6/2011 | Weisenburgh, II et al. | |
| 2011/0132965 A1 | 6/2011 | Moore et al. | |
| 2011/0139851 A1 | 6/2011 | McCuen | |
| 2011/0144640 A1 | 6/2011 | Heinrich et al. | |
| 2011/0147433 A1 | 6/2011 | Shelton, IV et al. | |
| 2011/0147434 A1 | 6/2011 | Hueil et al. | |
| 2011/0155781 A1 | 6/2011 | Swensgard et al. | |
| 2011/0155784 A1 | 6/2011 | Shelton, IV et al. | |

(56) References Cited

U.S. PATENT DOCUMENTS

| | | |
|---|---|---|
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |

FOREIGN PATENT DOCUMENTS

| | | |
|---|---|---|
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0 324 166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |

OTHER PUBLICATIONS

European Office Action dated Jul. 29, 2015, issued in EP Application No. 12745973.

Chinese Office Action dated Nov. 11, 2015, issued in Chinese Application No. 201280038896.1.

Chinese Office Action dated Jul. 15, 2016, issued in Chinese Application No. 201280038896.

* cited by examiner

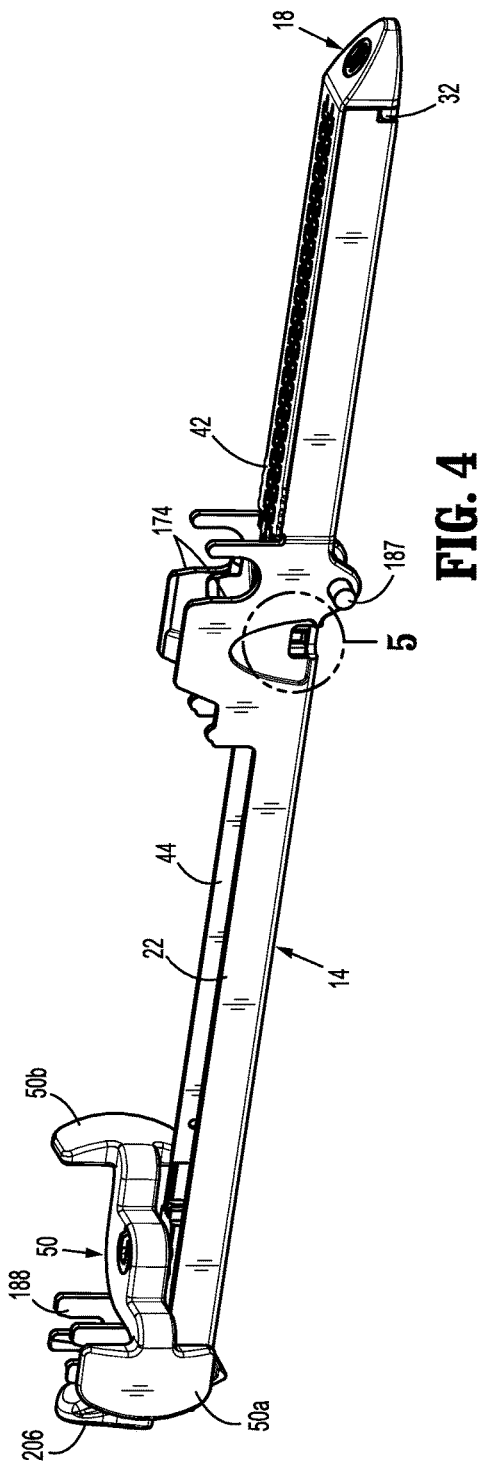
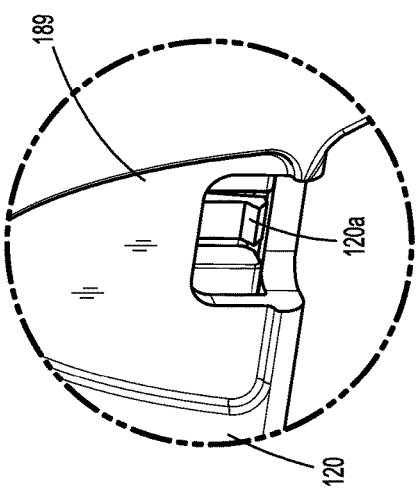
FIG. 4
FIG. 5

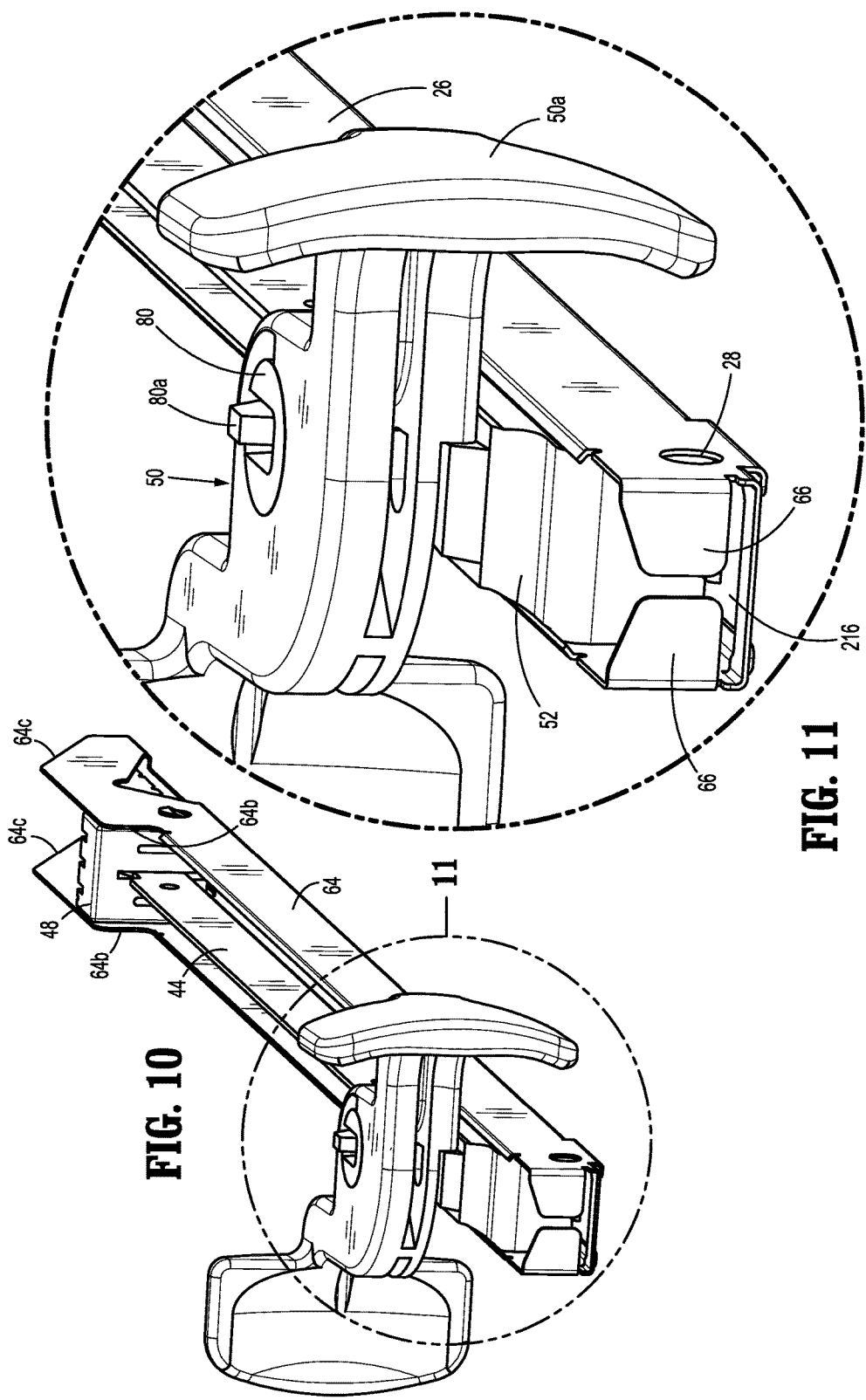

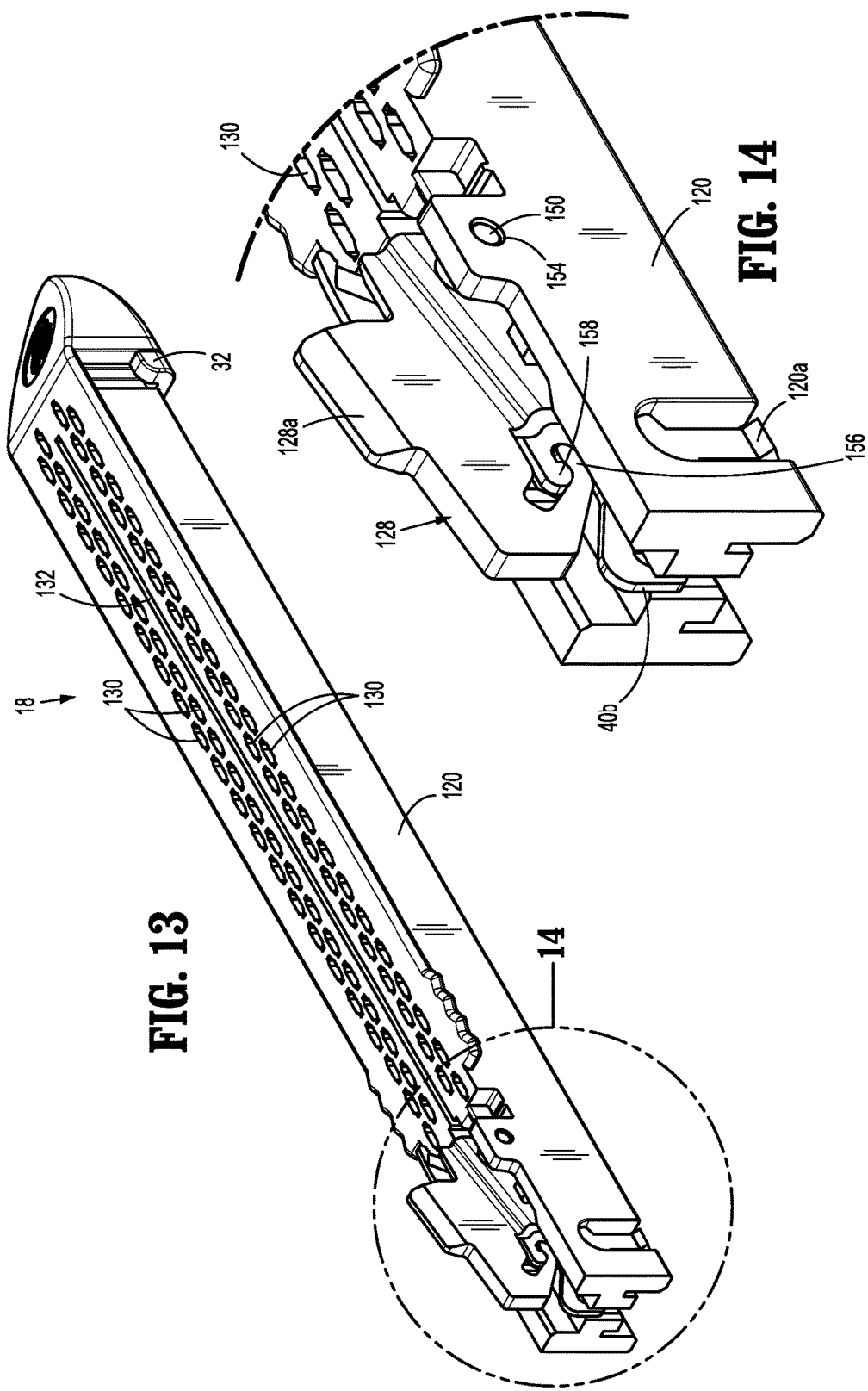

SURGICAL FASTENER APPLYING APPARATUS

This application is a continuation of U.S. patent application Ser. No. 13/546,976, filed Jul. 11, 2012, now U.S. Pat. No. 9,155,537, which claims priority from provisional application No. 61/521,074 filed, Aug. 8, 2011, the entire contents of which are incorporated herein by reference.

BACKGROUND

1. Technical Field

The present disclosure relates to a surgical fastener applying apparatus and, more particularly, to a surgical fastener applying apparatus having reusable and disposable components.

2. Discussion of Related Art

Surgical fastener applying apparatus, wherein tissue is first grasped or clamped between opposing jaw structures and then joined by means of surgical fasteners, are well known in the art. In some such apparatus, a knife is provided to cut the tissue which has been joined by the fasteners. The fasteners are typically in the form of surgical staples, although, other surgical fasteners may also be utilized, such as, for example, clips or two part polymeric surgical fasteners.

Surgical fastener applying apparatus typically include two elongated beam members which are used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the staples are driven from the cartridge assembly. Where two part fasteners are used, the beam member which includes the anvil carries a mating part of the two part fastener, e.g. the receiver. Generally, the staple formation process is affected by the interaction between one or more longitudinally moving camming members and a series of individual staple pushers. As the camming members travel longitudinally through the cartridge carrying beam member, the individual pusher members are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

Because of the dangers associated with improper sterilization, apparatus are typically disposable after use. Although the cartridge assembly may be replaced to perform multiple fastener applying operations on a single patient, the staple applying apparatus is typically disposable after a surgical procedure has been completed. This requirement of disposability may increase the costs associated with surgical procedures. Although reusable fastener applying apparatus have been developed, such apparatus can be overly complex and prove difficult to sterilize.

A need exists in the art for a fastener applying apparatus which includes reusable components, is not overly complex and is configured to facilitate proper sterilization after use in a surgical procedure.

SUMMARY

The present invention relates to a surgical fastener applying apparatus for applying surgical fasteners to tissue. In one aspect of the present disclosure, a surgical fastener applying apparatus is provided comprising an anvil half-section including a distal anvil portion and a proximal handle portion, a cartridge receiving half-section defining an elongated channel member, and a stationary housing. The stationary housing is configured to be releasably supported within the elongated channel member of the cartridge receiving half-section. The stationary housing supports firing components of the apparatus. The stationary housing is also dimensioned to releasably receive a single use loading unit. The stationary housing includes a lockout structure that prevents full insertion of the single use loading unit into the stationary housing after the stationary housing is mounted to the cartridge receiving half-section.

The lockout structure in some embodiments may define a first position which prevents insertion of the single use loading unit into the stationary housing, and a second position which allows insertion of the single use loading unit into the stationary housing. The lockout structure is configured to move between its first position and its second position. However, the lockout structure is obstructed from moving from the first position to the second position when the stationary housing positioned within the elongated channel member.

In one embodiment, the lockout structure is positioned on a central portion of the stationary housing. The lockout structure in some embodiments includes a pair of sidewalls and a pair of flanges extending from the top of each sidewall such that when the lockout structure is in the first position, the sidewalls are substantially parallel with respect to each other, and the flanges define a lateral dimension or opening therebetween which is less than the lateral dimension of the single use loading unit to prevent entry of the single use loading unit therein, and when the lockout structure is in the second position, the sidewalls are inclined away from each other, and the flanges define a lateral dimension or opening therebetween which is larger than the lateral dimension of the single use loading unit to permit entry of the single use loading unit therein.

In some embodiments, the sidewalls of the central portion are connected to proximal and distal portions of the stationary housing by live hinges, such that the sidewalls of the central portion are pivotable with respect to the proximal and distal portions. In other embodiments, the lockout structure includes a bottom surface, and the sidewalls are hingedly attached to the bottom surface.

In another aspect, the present disclosure provides a surgical fastener applying apparatus comprising a reusable anvil half-section, a reusable cartridge receiving half-section, and a disposing firing assembly configured to be releasably supported within the cartridge receiving half section. The firing assembly includes a disposable pusher assembly and a disposable single use loading unit operably mountable to the pusher assembly, wherein the single use loading unit is not operably mountable to the pusher assembly if the pusher assembly is mounted in the cartridge receiving half section.

In some embodiments, the surgical fastener apparatus further comprises first and second members extending from the pusher assembly movable between a first position having a first gap dimensioned to prevent insertion of the single use loading unit and a second position having a second gap larger than the first gap and dimensioned receive the single use loading unit. In some embodiments, the first and second members extend from first and second sidewalls of the pusher assembly. In some embodiments, the first and second members are normally in the second position.

In another aspect, the present disclosure provides a disposable firing assembly for use with a surgical fastener applying apparatus comprising a disposable single use loading unit and a disposable pusher assembly. The firing assembly is insertable into a cartridge receiving half section of the fastener applying apparatus and the single use loading unit is operably mountable to the pusher assembly, wherein the pusher assembly includes a lockout member movable from a first blocking position preventing operable insertion of the single use loading unit therein and a second position enabling operable insertion of the single use loading unit therein.

In some embodiments, the lockout member is biased to the first position, and the lockout member is prevented from moving to the second position when the pusher assembly is mounted within the cartridge receiving half section. In some embodiments, the lockout member includes first and second members extending inwardly toward a longitudinal axis of the pusher assembly and movable to vary a gap therebetween. In some embodiments, the first and second members pivot from a position substantially perpendicular to the longitudinal axis to a first position inclined with respect to the longitudinal axis.

BRIEF DESCRIPTION OF THE DRAWINGS

Various embodiments of the presently disclosed surgical fastener applying apparatus will now be described herein with reference to the accompanying figures wherein:

FIG. 4 is a side perspective view of the cartridge receiving half-section of the surgical fastener applying apparatus shown in FIG. 1 with the single use loading unit and the firing assembly supported within the cartridge receiving half-section;

FIG. 5 is an enlarged view of the indicated area of detail shown in FIG. 4;

FIG. 10 is a rear end perspective view from above of the firing assembly shown in FIG. 8;

FIG. 11 is an enlarged view of the indicated area of detail shown in FIG. 10;

FIG. 13 is a side perspective view of the SULU of the surgical fastener applying apparatus shown in FIG. 1;

FIG. 14 is an enlarged view of the indicated area of detail shown in FIG. 13;

FIG. 35A is a side cross-sectional view of a center portion of the stationary housing of FIG. 35 shown in a position that prevents insertion of the SULU therein;

FIG. 35B is a side cross-sectional view of a center portion of the stationary housing of FIG. 35 shown in a position that allows insertion of the SULU therein;

DETAILED DESCRIPTION OF EMBODIMENTS

Figure 1:
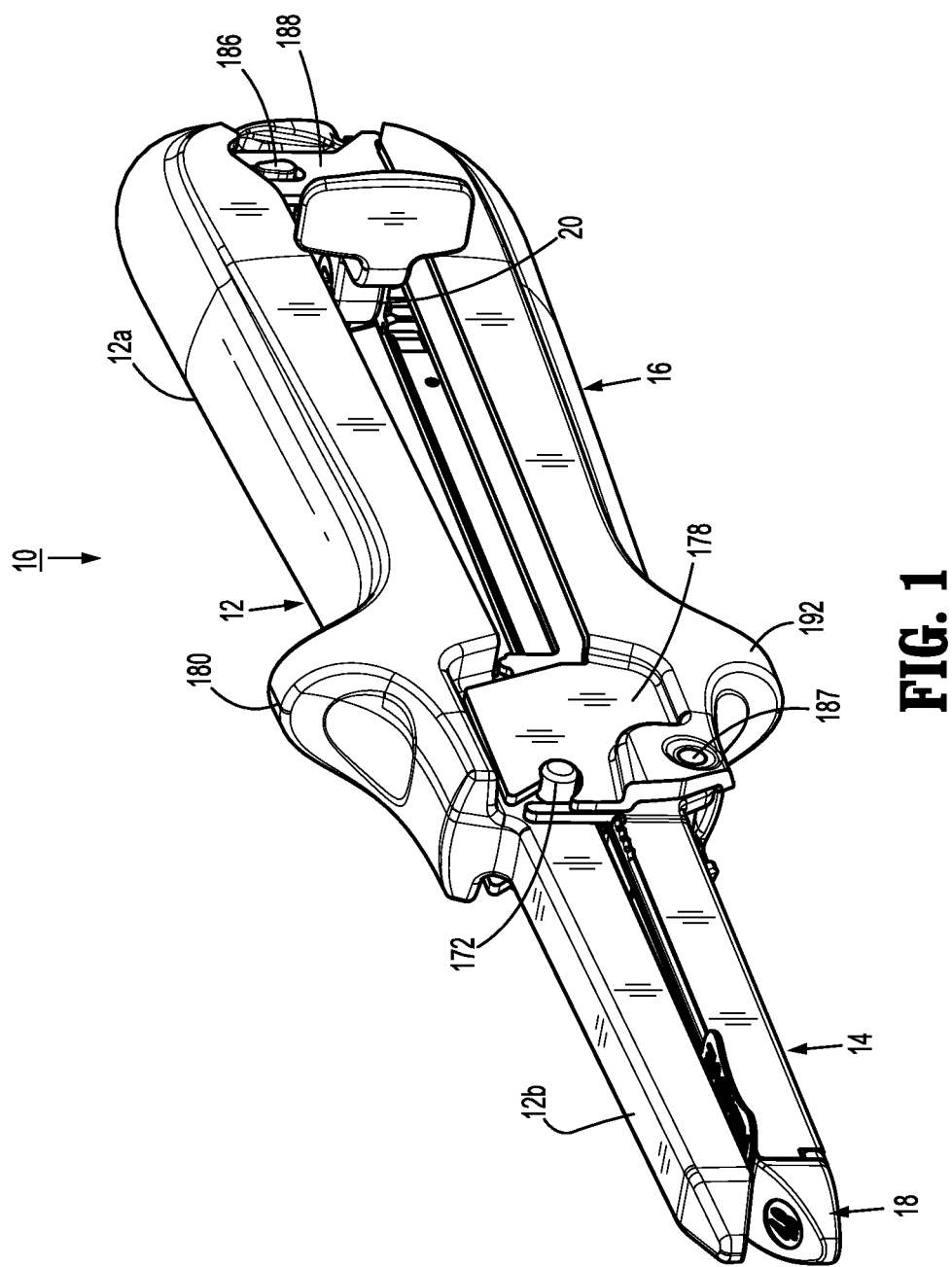
FIG. 1 is a side perspective view from the distal end of one embodiment of the presently disclosed surgical fastener applying apparatus in the clamped position.

Embodiments of the presently disclosed surgical fastener applying apparatus in accordance with the present disclosure will now be described in detail with reference to the drawings wherein like reference numerals identify similar or identical structural elements. As used herein, as is traditional, the term "proximal" refers to the end of the apparatus which is closer to the user and the term distal refers to the end of the apparatus which is further away from the user.

Figure 2:
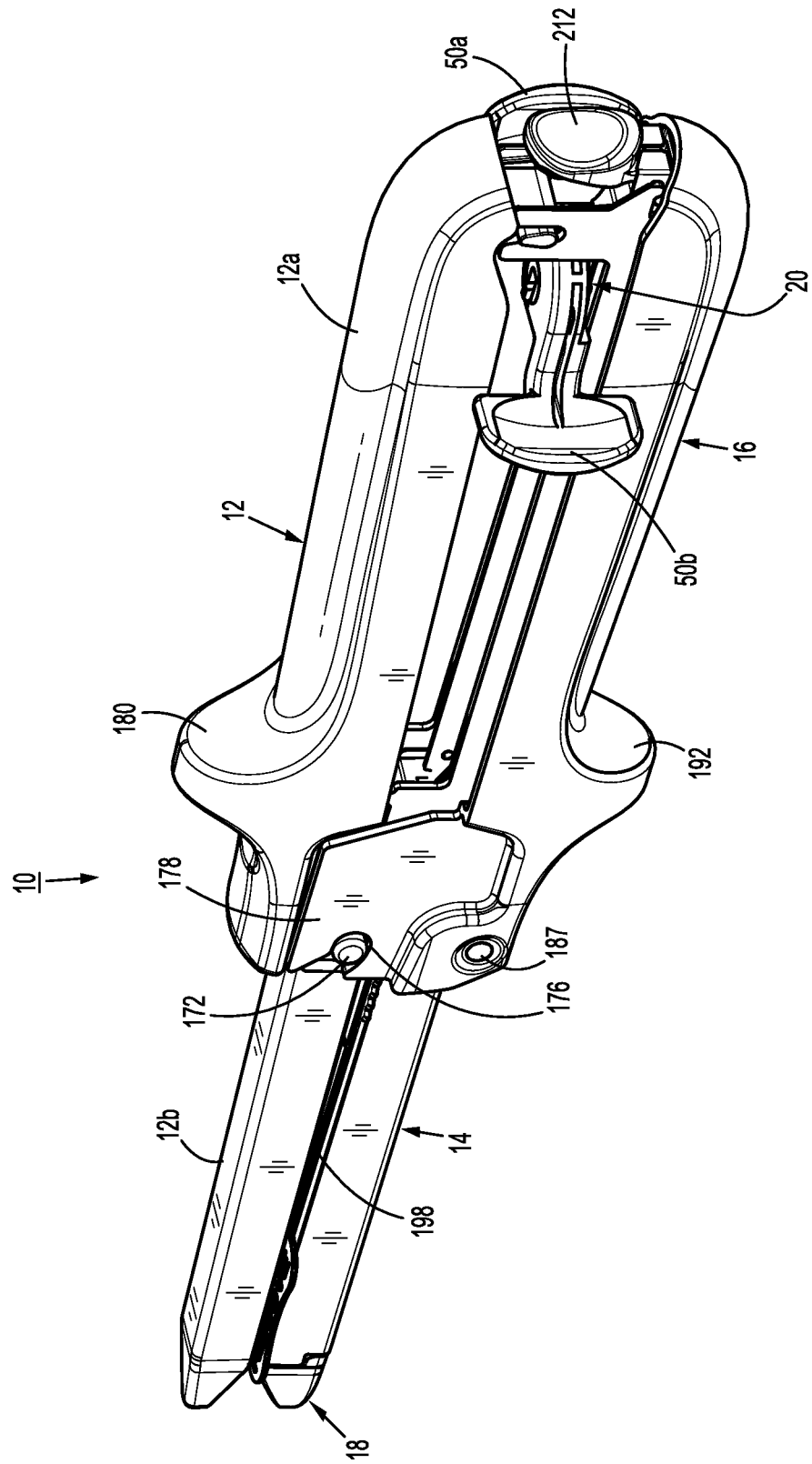
FIG. 2 is a side perspective view from the proximal end of the surgical fastener applying apparatus shown in FIG. 1 in the clamped position.
Figure 3:
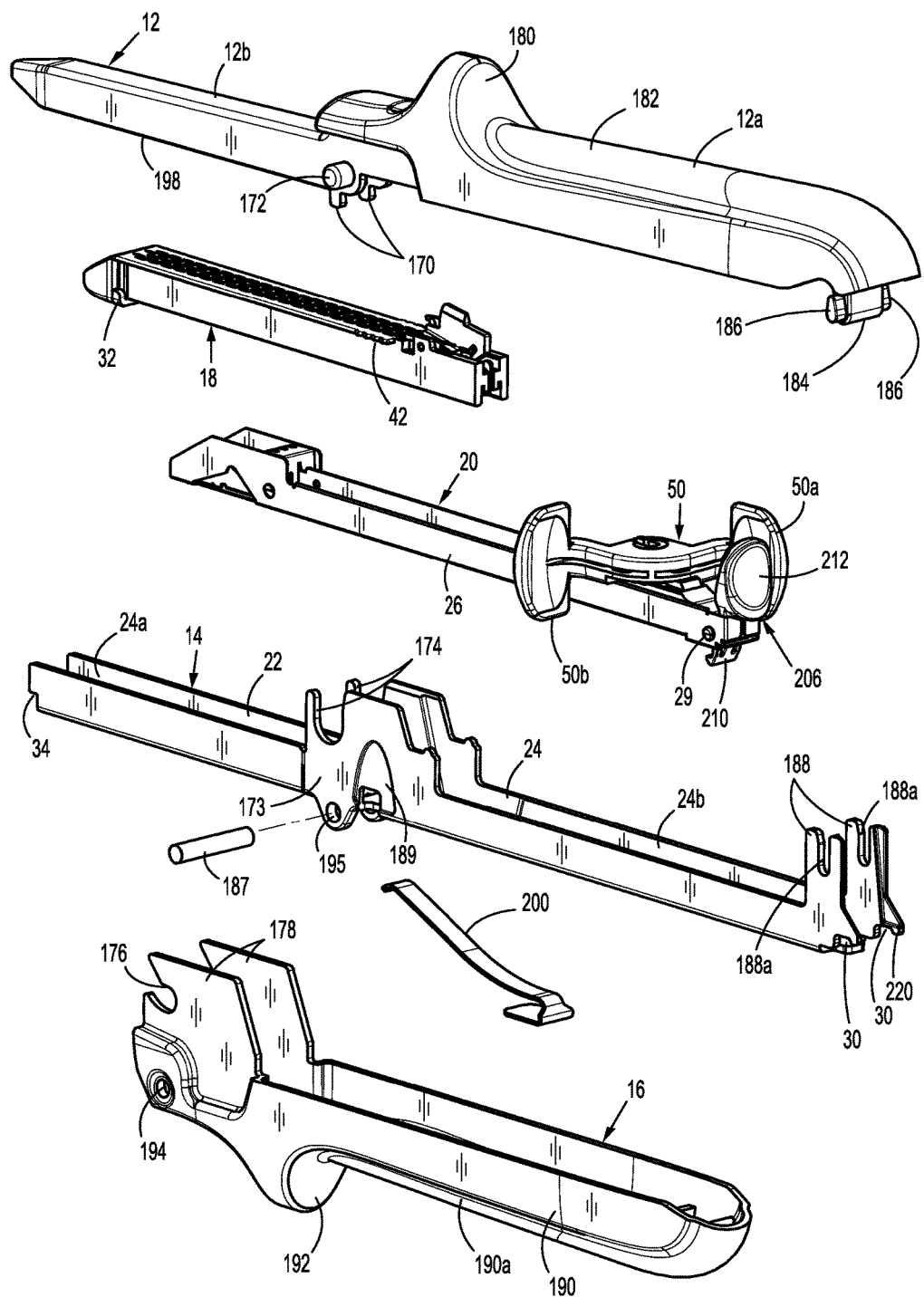
FIG. 3 is a side perspective view with parts separated of the surgical fastener applying apparatus shown in FIG. 1.

FIGS. 1-34 illustrate one embodiment of the presently disclosed surgical fastener applying apparatus designated generally as surgical stapler 10. Referring specifically to FIGS. 1-3, surgical stapler 10 includes an anvil half-section 12, a cartridge receiving half-section 14, a clamping lever 16, a single use loading unit 18 (hereinafter "SULU") and a firing assembly 20. In one embodiment, anvil half-section 12, cartridge receiving half-section 14 and clamping lever 16 are constructed to be reusable components and, as such, are constructed from a biocompatible material suitable for sterilization and repeated use, e.g., stainless steel. In contrast, SULU 18 and firing assembly 20 are constructed to be disposable and, as such, may be constructed from any suitable biocompatible material, e.g., plastics, metals, combinations thereof, having the requisite strength characteristics.

Figure 12:
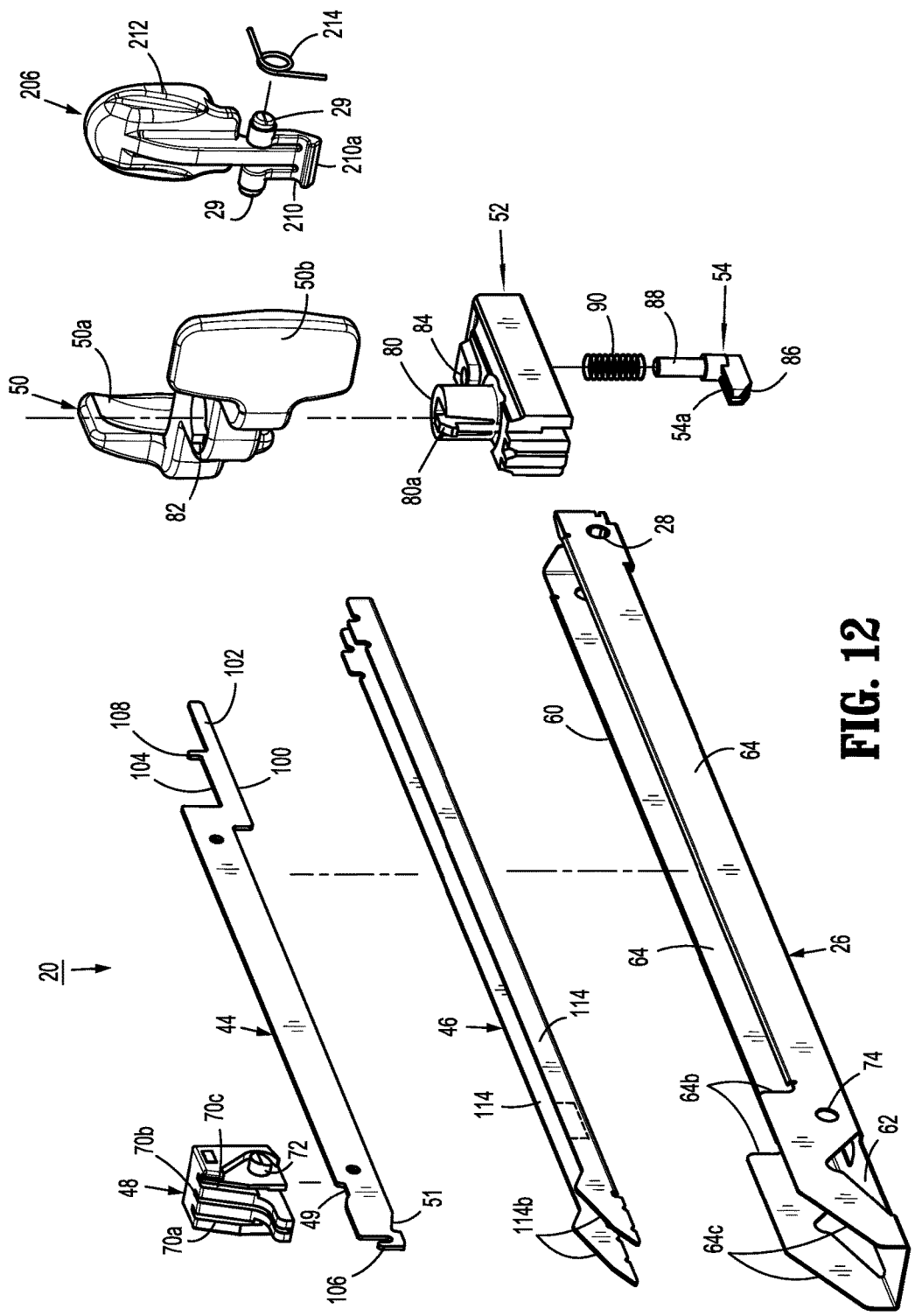
FIG. 12 is a side perspective view of the firing assembly shown in FIG. 10 with parts separated.

Referring to FIGS. 3-7, cartridge receiving half-section 14 defines an elongated channel member 22 which defines a substantially U-shaped channel 24 having a distal portion 24a dimensioned to releasably receive a SULU 18 and a proximal portion 24b dimensioned to releasably receive firing assembly 20. Firing assembly 20 includes a stationary housing 26 (see also FIG. 12) having a proximal end including openings 28 which receive ends of pivot members 29 (FIG. 12). Pivot members 29 pivotally support a locking member 206 on a proximal end of stationary housing 26 and extend through openings 28 into recesses 30 formed in a proximal portion of cartridge receiving half-section 14 to releasably secure the proximal end of firing assembly 20 within the proximal portion 24b of channel member 22 as will be discussed in further detail below. The distal end of firing assembly 20 defines a triangular cutout 64d. Cutout 64d is positioned to receive a protrusion 65 formed on an inner wall of channel member 22 (see FIGS. 9A-9C) to releasably secure the distal end of firing assembly 20 within channel member 22. The structure of firing assembly 20 will also be discussed in further detail below. Likewise, SULU 18 includes a pair of distal protrusions 32 which are positioned in cutouts 34 formed at the distal end of channel member 22 to releasably secure SULU 18 within the distal portion 24a of channel member 22. During assembly, firing assembly 20 must be inserted into proximal portion 24b of channel member 22 before SULU 18 is inserted into distal portion 24a of channel member 22 as will be discussed below. To position SULU 18 in channel member 22, protrusions 32 on SULU 18 are positioned within cutouts 34 while SULU 18 is positioned above and at an angle to channel member 22. Thereafter, SULU 18 can be rotated downwardly into distal portion 24a of U-shaped channel 24. This allows for the drive components of firing assembly 20 to properly align with components of SULU 18 and also facilitates engagement of the firing assembly 20 with a knife 40 (FIG. 17) supported within SULU 18. A proximal end of SULU 18 includes an outwardly extending serrated surface 42 (FIG. 7) to facilitate gripping of the proximal end of SULU 18 to allow for removal and/or replacement of SULU 18 from channel member 22. Prior to movement of stapler 10 to the clamped position, as will be discussed below, serrated gripping surface 42 will not fully seat within distal portion 24a of channel member 22.

Referring to FIGS. 8-12, firing assembly 20 includes stationary housing 26, a knife actuating bar 44, a cam bar 46, a guide block 48, a firing lever 50, a slide block 52, a pedal 54 and the pivotal locking member 206 (FIG. 12). In one embodiment, stationary housing 26 includes a U-shaped frame 60 including a bottom wall 62 and a pair of sidewalls 64. The distal end of each sidewall 64 defines a proximal step 64b, a distal angled portion 64c (FIG. 9) and the triangular cutout 64d. As discussed above, triangular cutout 64d is positioned to receive the protrusion 65 (FIG. 9B) formed on an inner wall of channel member 22. A proximal end of each sidewall 64 includes a pair of transversely extending deformable wall portions 66 (FIG. 11) which are spaced from a proximal end of slide block 52 and define an area between wall portions 66 and slide block 52 for pivotally receiving locking member 206 as will be discussed in further detail below.

Figure 9:
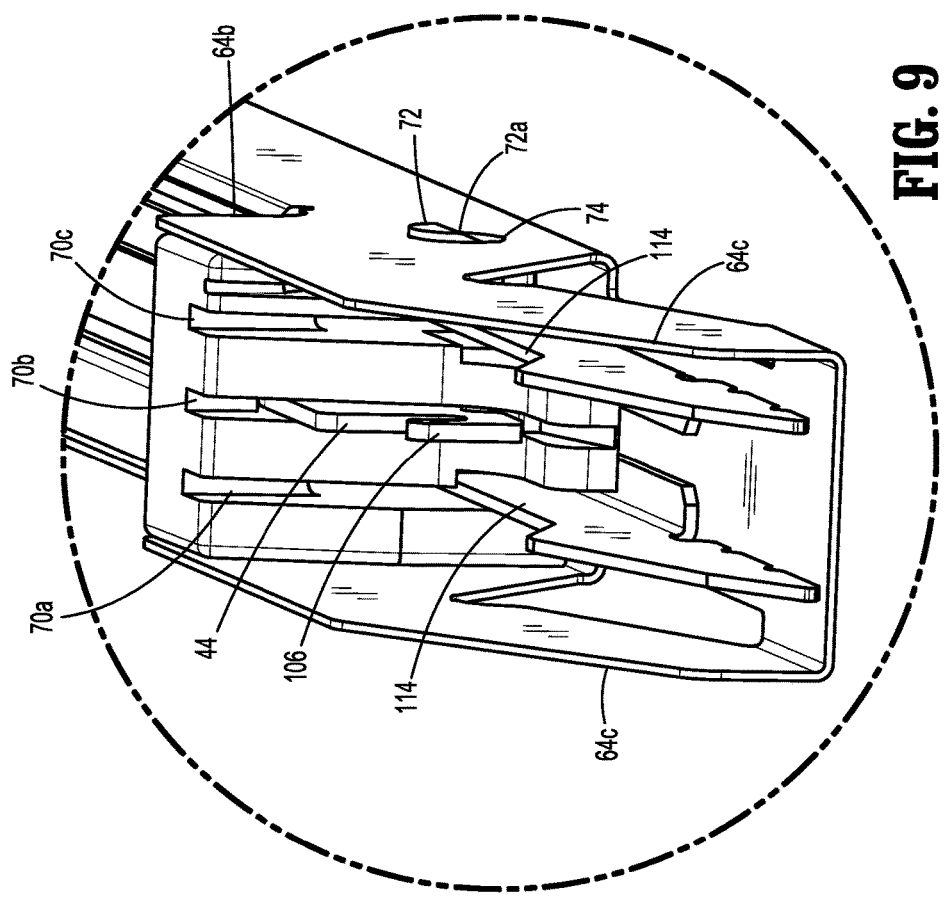
FIG. 9 is an enlarged view of the indicated area of detail shown in FIG. 8.
Figure 8:
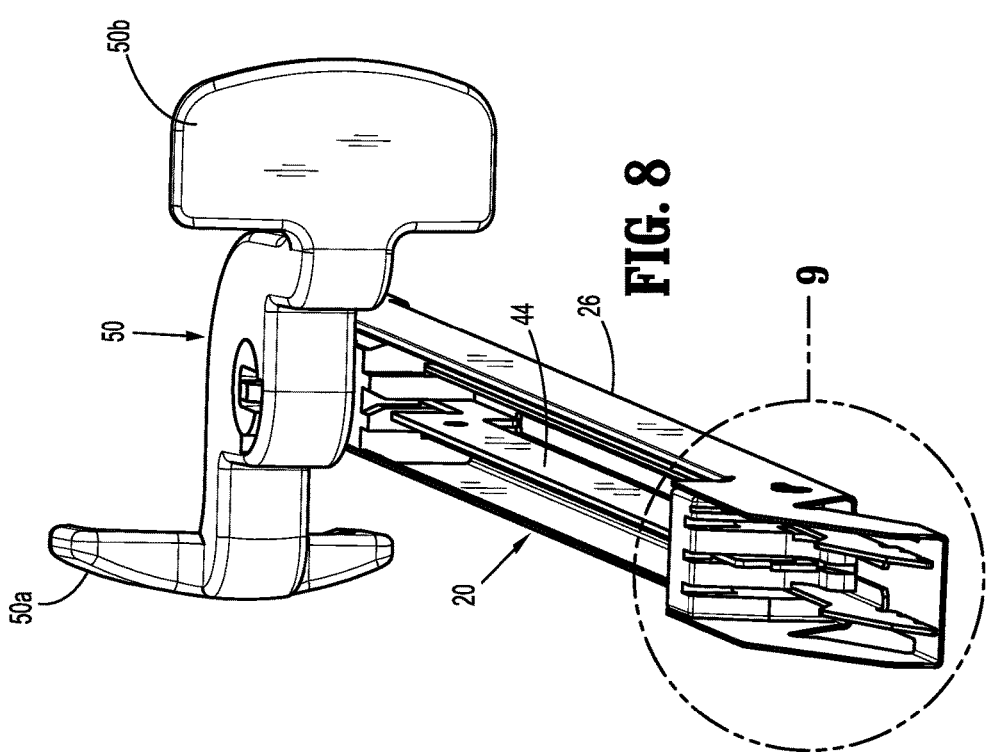
FIG. 8 is a front end perspective view from above the firing assembly of the surgical fastener applying apparatus shown in FIG. 3.
Figure 9B:
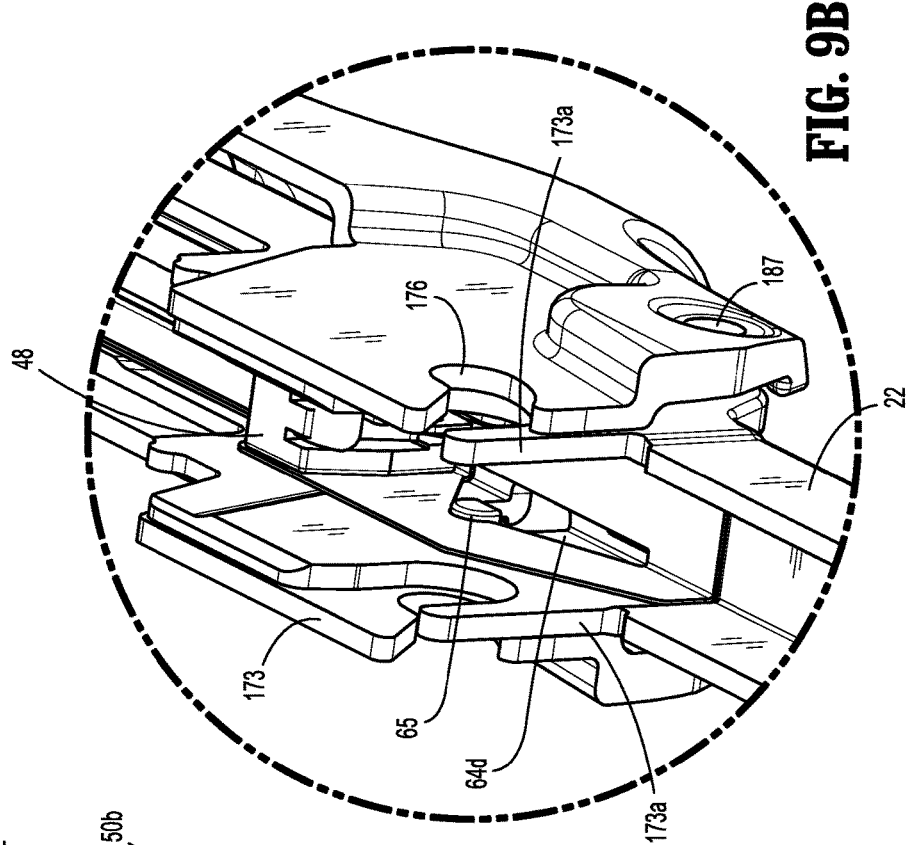
FIG. 9B is an enlarged view of the indicated area of detail shown in FIG. 9A.
Figure 9A:
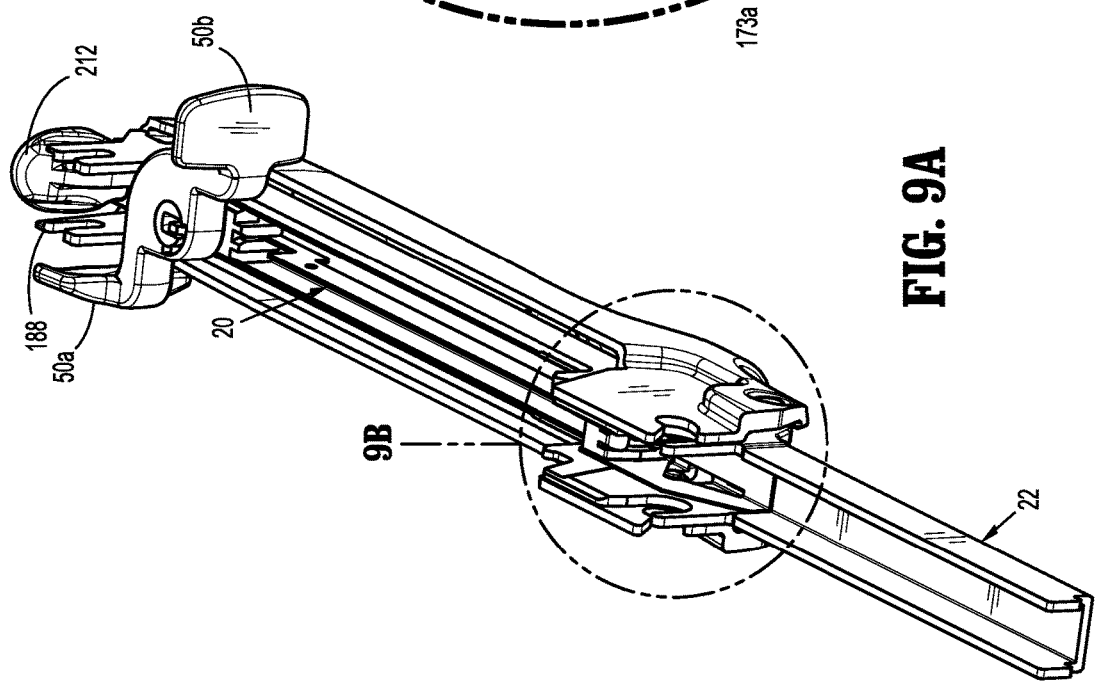
FIG. 9A is a top, perspective view of the channel member with the firing assembly releasably secured therein.
Figure 9C:
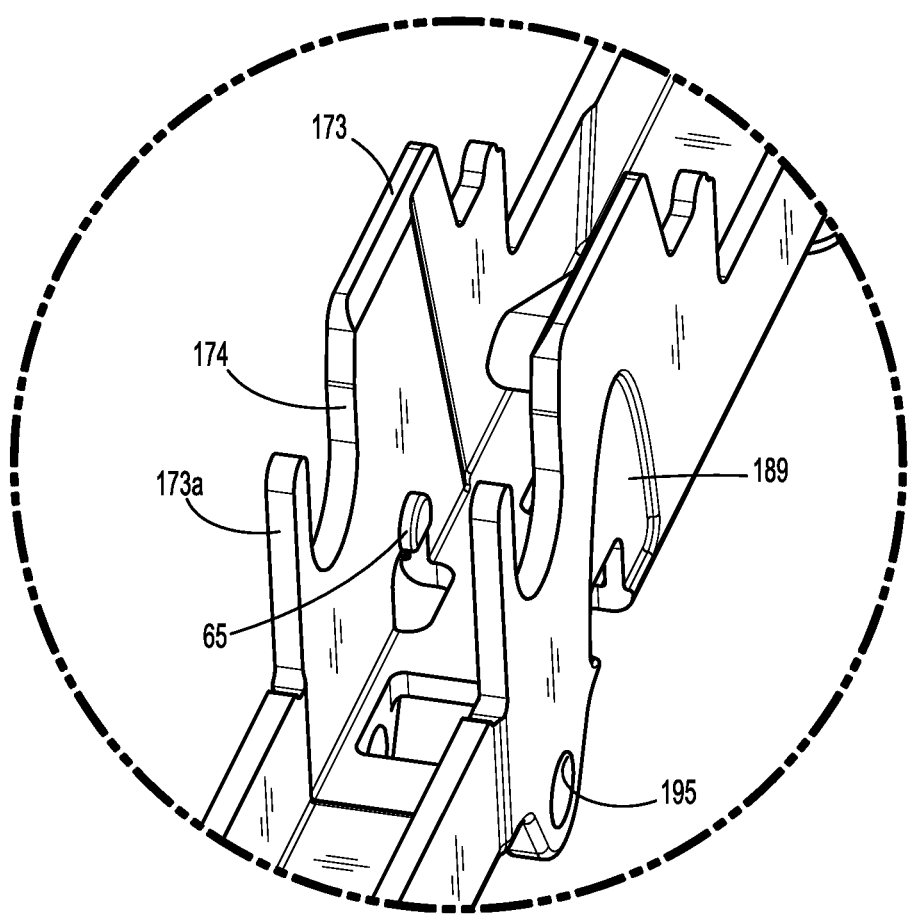
FIG. 9C is a top, perspective view of a central portion of the channel member.

Guide block 48 includes a body defining three longitudinal slots 70a-c and a pair of outwardly extending protrusions 72. In one embodiment, each protrusion 72 is substantially cylindrical and includes a tapered portion 72a (FIG. 9). Alternately, other protrusion configurations are envisioned. Protrusions 72 are dimensioned to be received in openings 74 (FIG. 12) formed in sidewalls 64 of stationary housing 26 to axially fix guide block 48 within the distal end of stationary housing 26. Protrusions 72 allow for a degree of pivotal movement of guide block 48 within U-shaped frame 60. As will be discussed in further detail below, guide block 48 is pivotal from a first position (FIG. 19) in locking engagement with notches 49 and 51 of knife actuating bar 44 to a second position (FIG. 26) disengaged from notches 49 and 51 of knife actuating bar 44 in response to movement of stapler 10 to the clamped position. A torsion spring is provided about protrusion 72 to urge guide block 48 into locking engagement with notches 49 and 51. Each of slots 70a and 70c is dimensioned to slidably receive a respective sidewall 114 of cam bar 46. Similarly, slot 70b is dimensioned to slidably receive knife actuating bar 44.

Figure 20:
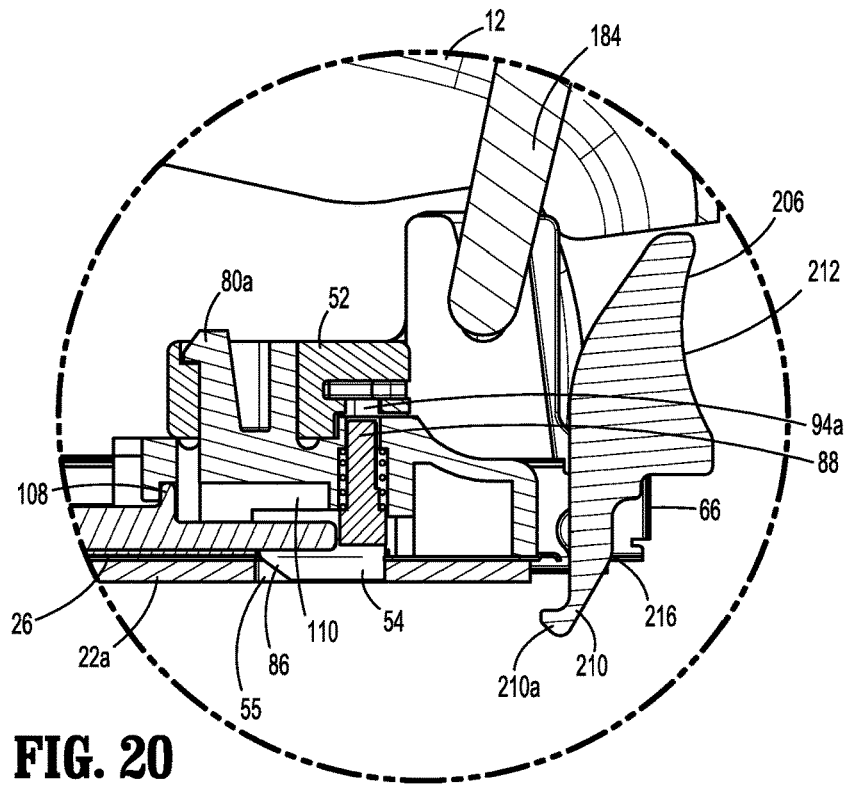
FIG. 20 is an enlarged view of the indicated area of detail shown in FIG. 18.

Slide block 52 includes a hub 80 which includes a resilient finger 80a configured to be snap-fit into a pivot hole 82 formed in firing lever 50. Firing lever 50 is pivotal about hub 80 when the slide block 52 is in a retracted position to facilitate actuation of the firing assembly 20 from either side of stapler 10. Pedal 54 is reciprocally received within a hole 84 formed in slide block 52. Pedal 54 includes a split body portion 54a which is configured to straddle a proximal end 102 of knife actuating bar 44. In one embodiment, split body portion 54a includes an angled distal surface 86. A pin 88 extends upwardly from pedal 54 through hole 84 in slide block 52. A biasing member 90 is positioned between split body portion 54a and slide block 52, about pin 88 to urge pedal 54 downwardly away from slide block 52 to an extended position. In the retracted position of slide block 52, pedal 54 is received in a cutout 55 formed in a bottom wall 22a of channel member 22 (FIG. 20).

Figure 30:
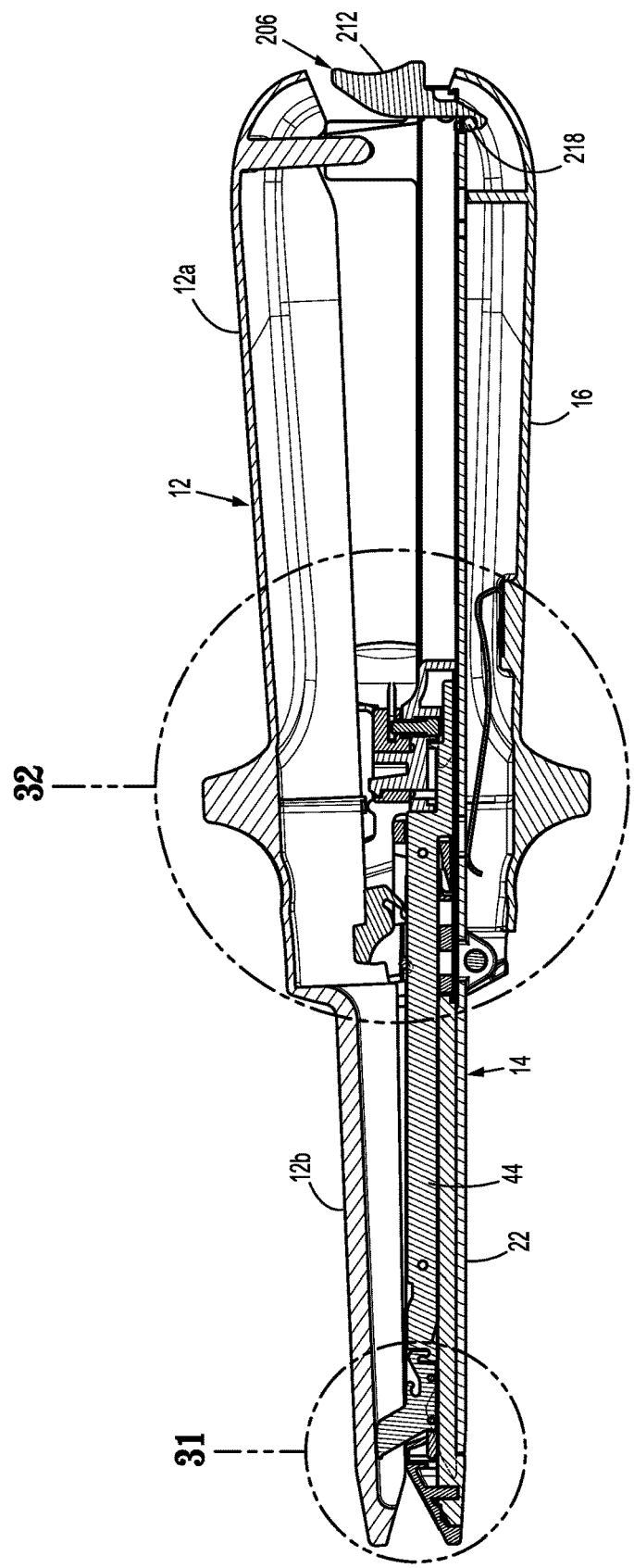
FIG. 30 is a side cross-sectional view of the surgical fastener applying apparatus shown in FIG. 29 with the firing assembly in the actuated position.

Firing lever 50 includes first and second finger engagement members 50a and 50b, either one of which can be selectively engaged to move the firing lever 50 through a firing stroke from either side of stapler 10. An arcuate recess 94 (FIG. 12B) is formed in a bottom surface of firing lever 50 which slidably receives pin 88 of pedal 54 to define the range of rotation through which firing lever 50 can pivot about hub 80 of slide block 52. As used herein, a firing stroke is defined as movement of firing lever 50 from a fully retracted position (FIG. 25) to a fully advanced position (FIG. 30). A stop recess 94a is formed at each end of arcuate recess 94. Stop recesses 94a are configured and dimensioned to receive the end of pin 88 of pedal 54 to prevent pivotal movement of firing lever 50 about hub 80 during a firing stroke of surgical stapler 10. More specifically, when the firing assembly 20 is actuated to advance slide block 52 distally within stationary housing 26, angled distal surface 86 of pedal 54 engages channel member 22 and is cammed out of cutout 55 (FIG. 27) to urge pin 88 upwardly into a stop recess 94a to prevent pivotal movement of firing lever 50 during movement of firing lever 50 through a firing stroke. As is evident, pin 88 must be positioned beneath a stop recess 94a to allow pedal 54 to lift upwardly from cutout 55 to allow firing lever 50 to be moved through the firing stroke. Thus, firing lever 50 must be pivoted to one side or the other of firing assembly 20 before the firing lever 50 can be moved through a firing stroke.

Figure 27:
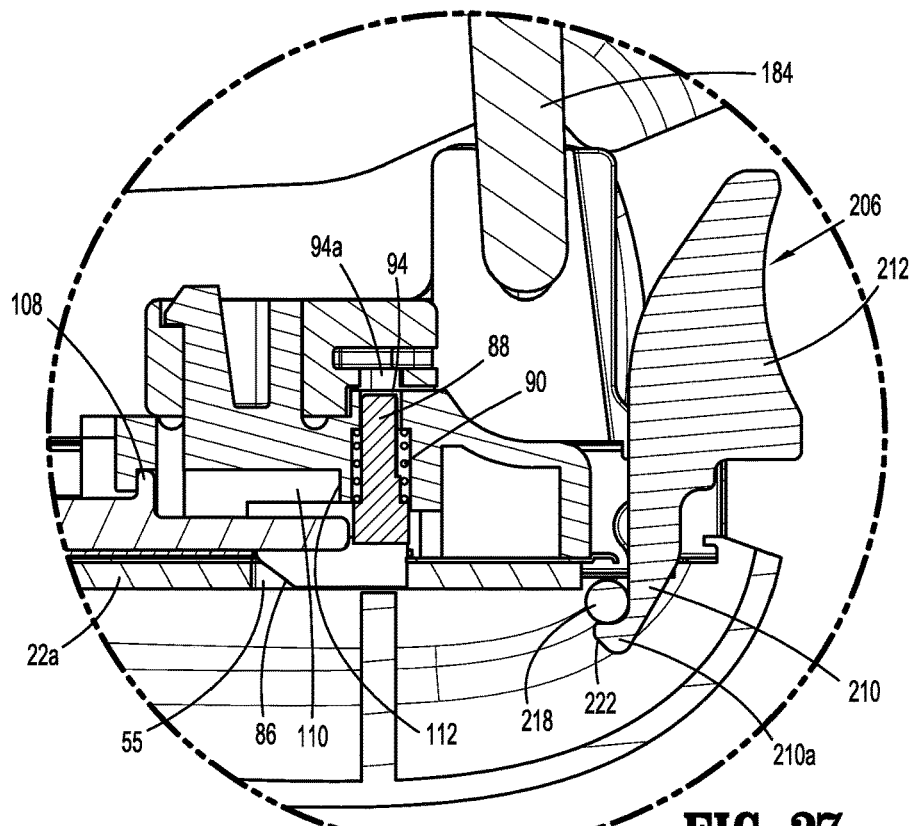
FIG. 27 is an enlarged view of the indicated area of detail shown in FIG. 25.

Knife actuating bar 44 includes a proximal end having a stepped portion 100 which includes a proximal first step 102 having a first height and a second step 104 having a second height which is greater than the first height. A distal end of actuating bar 44 includes an upturned hook portion 106 and upper and lower notches 49 and 51. A finger 108 projects upwardly from knife actuating bar 44 between first and second steps 102 and 104. As shown in FIG. 27, finger 108 is slidably received within a recess 110 formed in an underside of slide block 52. When slide block 52 is advanced distally within stationary housing 26, finger 108 moves within recess 110 such that slide block 52 moves in relation to knife actuating bar 44 until finger 108 engages a wall 112 (FIG. 32) defining a proximal end of recess 110. When finger 108 engages wall 112, further distal movement of slide block 52 will also effect distal movement of knife actuating bar 44. As will be evident below, this arrangement allows for staples to be ejected from SULU 18 prior to cutting of tissue.

Figure 12A:
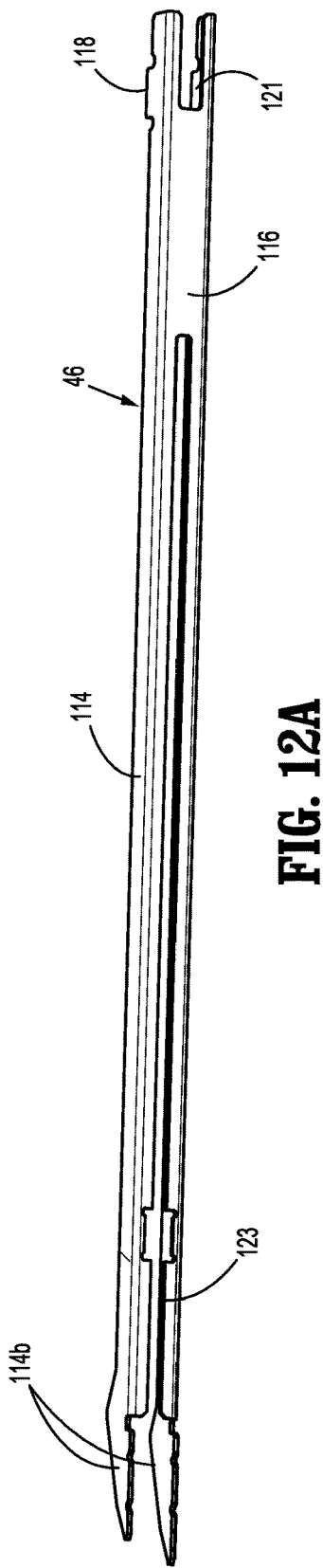
FIG. 12A is a bottom perspective view of the cam bar of the firing assembly shown in FIG. 12.
Figure 12B:
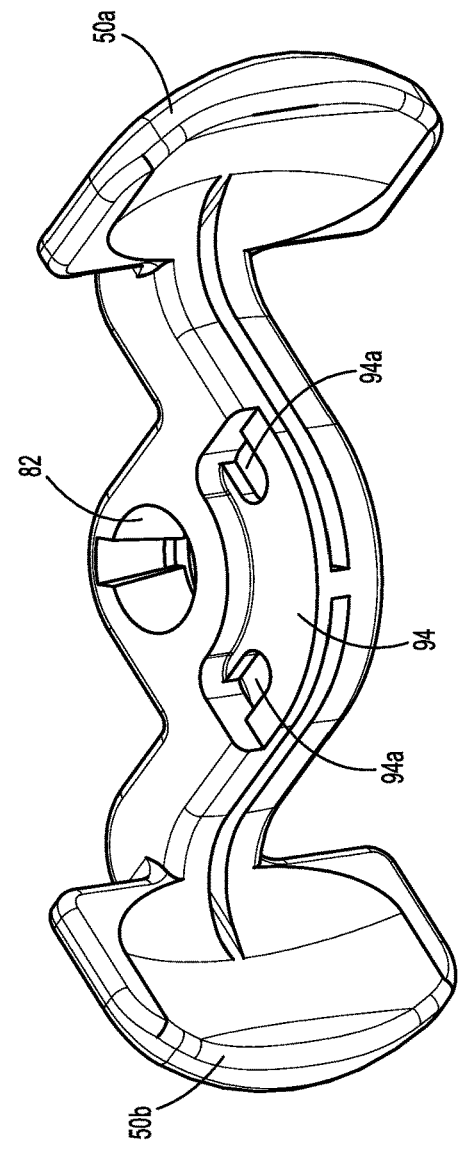
FIG. 12B is a bottom perspective view of the firing lever of the firing assembly shown in FIG. 12.
Figure 16:
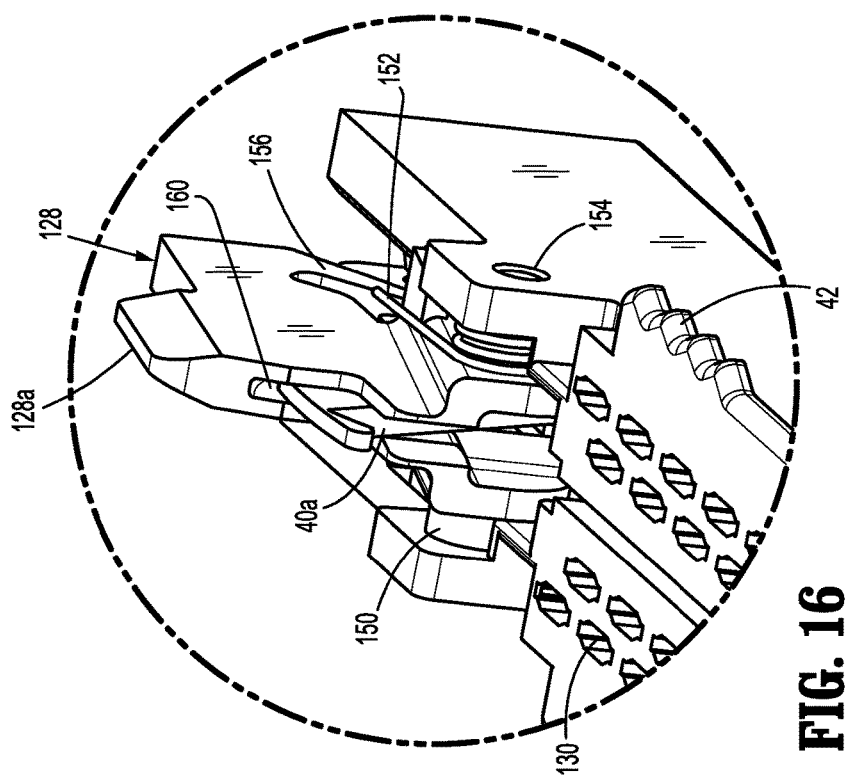
FIG. 16 is an enlarged view of the indicated area of detail shown in FIG. 15.
Figure 15:
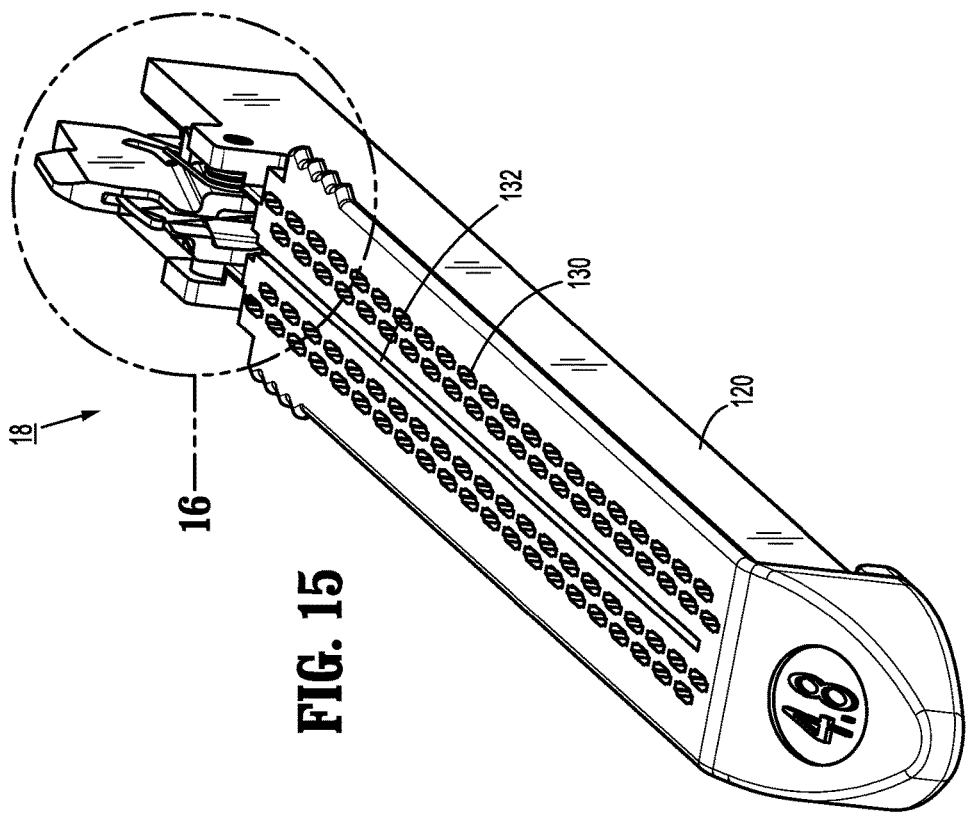
FIG. 15 is a front perspective view of the SULU shown in FIG. 13.

Referring to FIGS. 12 and 12A, cam bar 46 includes a pair of sidewalls 114 and a base wall 116 (FIG. 12A). The proximal end 114a of each sidewall 114 includes a raised wall portion 118. Each raised wall portion 118 is configured to be fixedly received in a slot (not shown) formed in an underside of slide block 52 to fixedly secure the proximal end of cam bar 46 to slide block 52. Alternately, slide block 52 may be molded about the proximal end of knife actuating bar 44. The distal end of each sidewall 114 includes an angled camming surface 114b. Base wall 116 defines a distally extending elongated slot 123 (FIG. 12A) which extends from the distal end of cam bar 46 along a substantial length of the cam bar 46 and a proximally extending longitudinal slot 121. Slot 121 is positioned to facilitate the passage of pedal 54 through cutout 55 of channel member 22 when slide block 52 is in the retracted position. See FIG. 27.

Sidewalls 114 of cam bar 46 are slidably positioned in slots 70a and 70c of guide block 48 and knife actuating bar 44 is slidably positioned in longitudinal slot 70b of guide block 48. When firing assembly 20 is supported in channel member 22 and firing lever 50 is pivoted to one side of stationary housing 26 and pushed distally, slide block 52 is moved distally within stationary housing 26. As slide block 52 begins to move distally, tapered surface 86 of pedal 54 engages a proximal edge of channel member 22 defining cutout 55 to urge pedal 54 upwardly out of cutout 55, through slot 121 of cam bar 46, and onto an inner surface of stationary housing 26 of firing assembly 20 (FIG. 27). As this occurs, pin 88 of pedal 54 moves into a stop recess 94a to prevent further pivotal movement of firing lever 50. If firing lever 50 is not pivoted to a position in which pin 88 is positioned beneath a stop recess 94a, pedal 54 will be prevented from moving upwardly out of cutout 55 and firing lever 50 will be prevented from moving through a firing stroke. As firing lever 50 is moved distally, finger 108 moves within recess 110 such that knife actuating bar 44 remains stationary as cam bar 46 is advanced distally. When finger 108 engages proximal wall 112 defining recess 110, knife actuating bar 44 is moved distally with slide block 52 and cam bar 46. As will be discussed below, when cam bar 46 and knife actuating bar 44 are moved distally within stationary housing 26 of firing assembly 20 and channel member 22, angled camming surfaces 114b of cam bar 46 are moved through SULU 18 to eject fasteners from SULU 18. Simultaneously, although with a preset delay equal to the length of recess 110 (FIG. 32), knife actuating bar 44 drives a knife blade 40 through SULU 18 to dissect tissue.

U.S. Pat. No. 7,631,794 ("the '794 patent") discloses a surgical fastener applying apparatus which includes a firing assembly similar to that described above. The '794 patent is incorporated herein by reference in its entirety.

Figure 17:
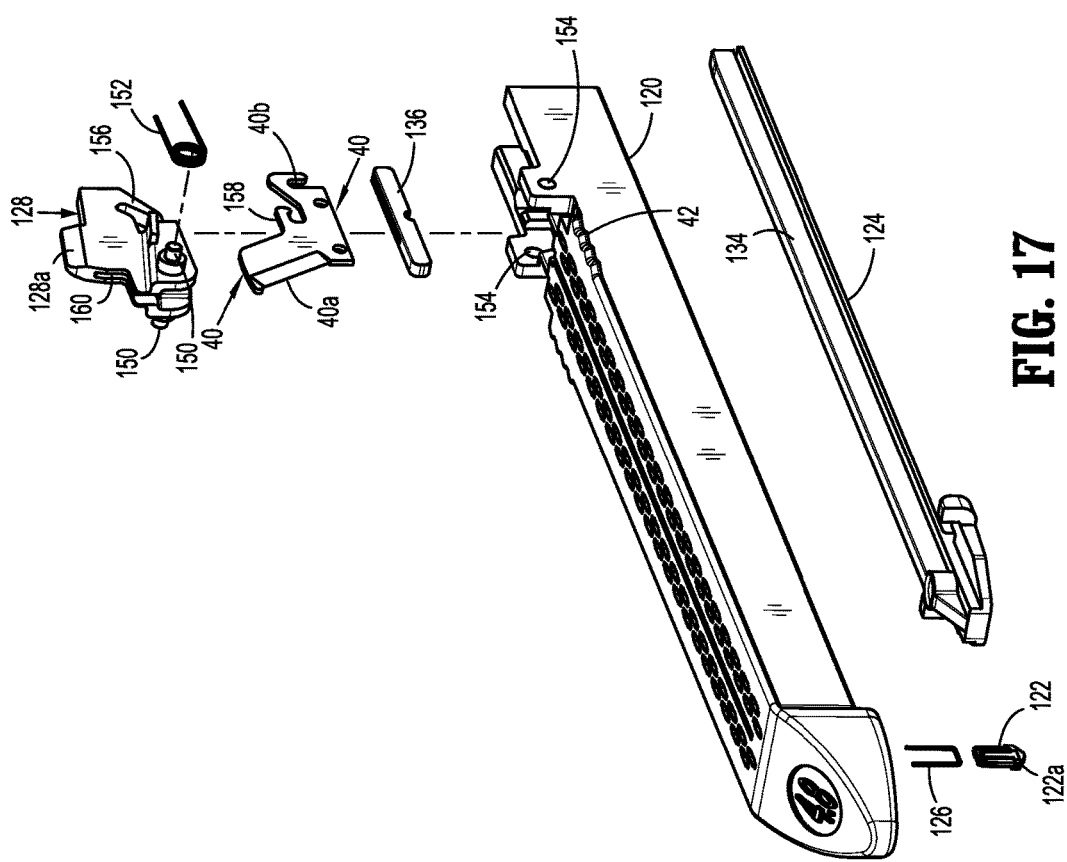
FIG. 17 is a side perspective view with parts separated of the SULU shown in FIG. 15.
Figure 18:
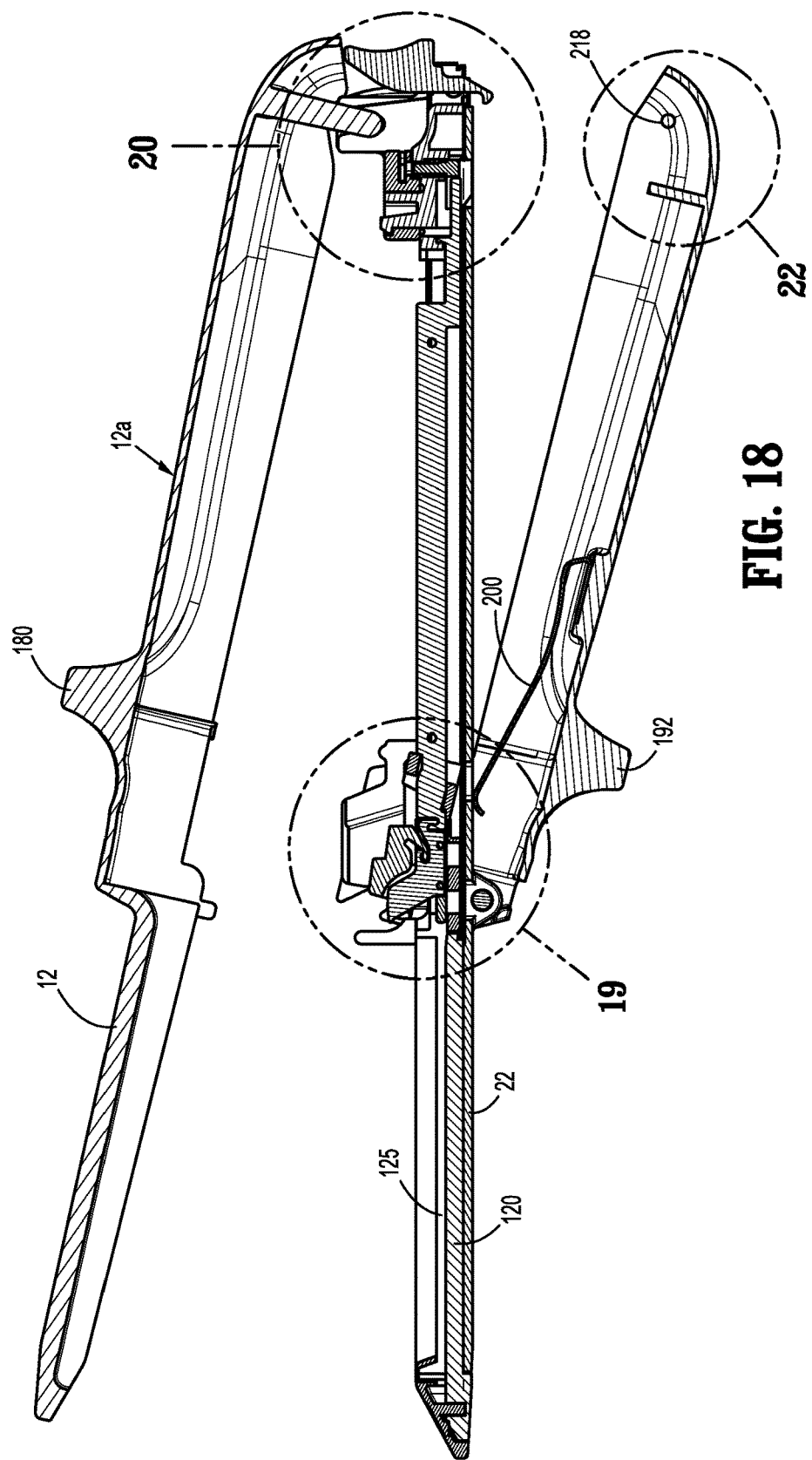
FIG. 18 is a side cross-sectional view of the surgical fastener applying apparatus shown in FIG. 1 in the open position.

FIGS. 13-17 illustrate SULU 18. Referring to FIG. 17, SULU 18 includes a body 120, a plurality of staple pushers 122 (only one is shown), a bottom cover 124, a knife 40 having an angled sharpened leading edge or blade 40a, a plurality of staples 126 (only one is shown), and a pivotally mounted safety lockout 128. A proximal end of body 120 includes a flexible finger 120a which projects slightly beyond the outer wall defining body 120. Finger 120a frictionally engages an inner wall of channel member 22 to retain the proximal end of SULU 18 within channel member 22 when SULU 18 is releasably positioned within channel member 22. As is known in the art, body 120 has a plurality of rows of staple retaining slots 130, e.g., four, six, etc. and a linear slotted knife track 132 centrally disposed in body 120. Surgical stapler 10 can be dimensioned to receive or accommodate SULU's of different staple line lengths including, e.g., 60 mm, 80 mm and 100 mm. Knife 40 includes a downturned hook portion 40b which is positioned to engage upturned hook portion 106 (FIG. 12) of knife actuating bar 44 when SULU 18 is positioned within channel member 22.

In the illustrated embodiment, body 120 includes two staggered rows of slots 130 formed on either side of linear slotted knife track 132. The staggered rows of slots 130 extend beyond the distal end of knife track 132 to facilitate staple formation beyond the distal end of the stroke of the knife blade 40.

Staple pushers 122 may be configured to extend into one or more slots 130. In one embodiment, a single pusher is associated with each slot 130. Alternately, as illustrated in FIG. 17, each pusher 122 can be configured to extend into two adjacent slots 130 and is positioned beneath respective staples 126 which are retained in slots 130. As is known in the art, each pusher 122 includes a lower cam surface 122a which is positioned to engage one of cam surfaces 114b (FIG. 12) on the distal end of cam bar 46 such that movement of cam bar 46 through SULU 18 sequentially lifts each respective pusher 122 within its respective slot or slots 130 to eject staples from slots 130.

Bottom cover 124 partially encloses a channel 125 (FIG. 18) formed within the cartridge body 120. A longitudinal ridge 134 is formed on an upper surface of bottom cover 124 and provides a bearing surface for a knife supporting member 136 which is secured to a bottom edge of knife 40. Knife 40 may be secured to supporting member 136 via pins, welding or other known fastening techniques. During a firing stroke, knife 40 is guided along knife track 132 as the firing lever 50 is advanced through channel member 22. A pair of slots 138 is defined between the sides of ridge 134 and an outer wall of cartridge body 120. Longitudinal ridge 134 is positioned within body 120 and dimensioned to be slidably received in elongated slot 120 (FIG. 12A) of cam bar 46 such that cam bar 46 is slidably movable through cartridge body 120 about longitudinal ridge 134 to eject staples 126 from SULU 18.

Figure 19:
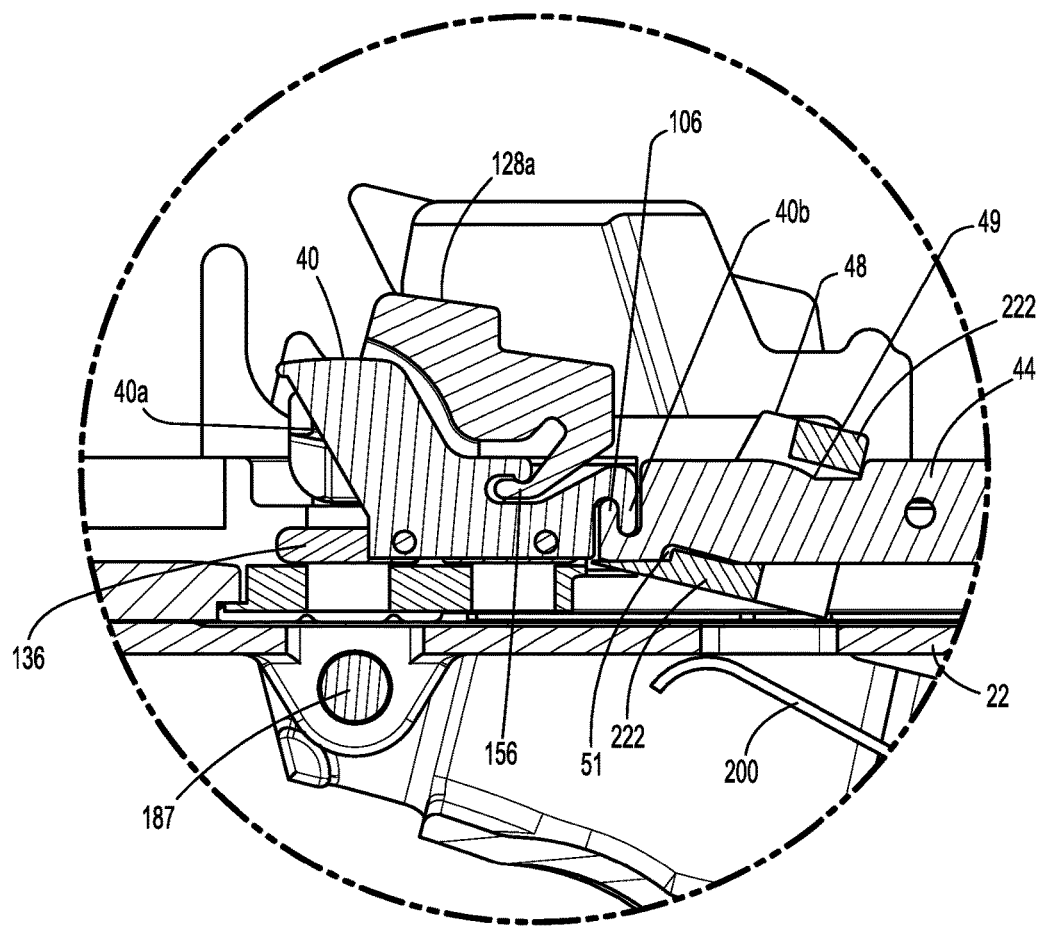
FIG. 19 is an enlarged view of the indicated area of detail shown in FIG. 18.
Figures 33, 34:
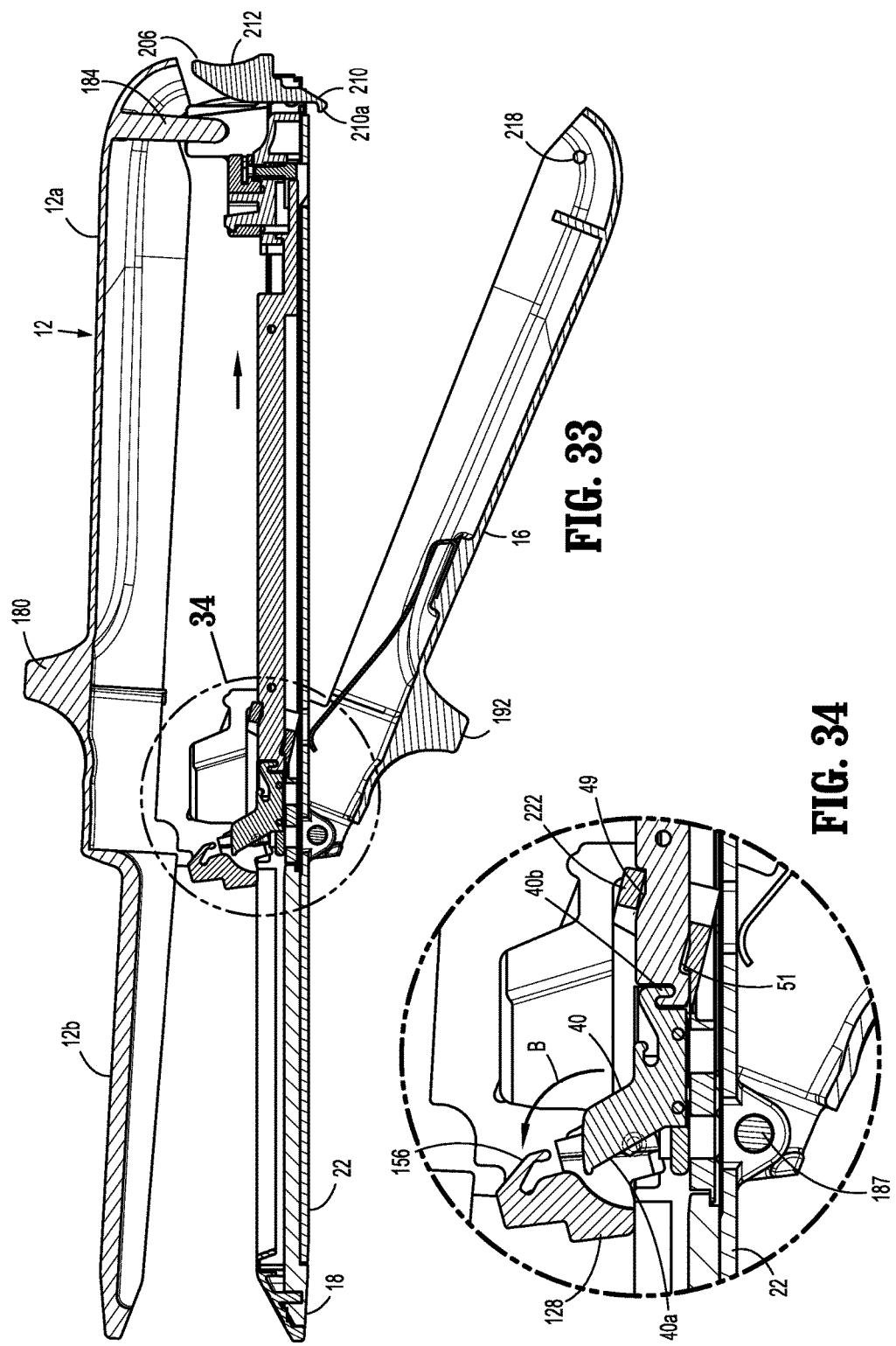
FIG. 33 is a side cross-sectional view of the surgical fastener applying apparatus shown in FIG. 1 after the apparatus has been fired and moved to the open position.
FIG. 34 is an enlarged view of the indicated area of detail shown in FIG. 33.

Safety lockout 128 is pivotally disposed on an upper proximal end of body 120 and is pivotal about a pivot member 150 from a locked orientation (FIG. 26) to unlocked orientation (FIG. 34). Pivot member 150 is received in openings 154 in body 120. A biasing member, e.g., spring 152, is positioned between knife supporting member 136 and safety lockout 128 to urge safety lockout 128 towards the unlocked orientation. Safety lockout 128 includes a proximal hook 156 which is positioned to receive an engagement member 158 formed on the knife 40 to retain the safety lockout 128 in the locked orientation when the knife 40 is in the retracted position (FIG. 19). When the knife 40 is moved towards the advanced position during a firing stroke, engagement member 158 is moved away from proximal hook 156 to allow safety lockout 128 to pivot towards the unlocked position in response to the urging of spring 152. It is noted that safety lockout 128 is prevented from pivoting to the unlocked position when the anvil half-section 12 and cartridge receiving half-section 14 are in the clamped position because the top surface 128a of safety lockout 128 engages an inner surface of anvil half-section 12 to prevent pivoting of safety lockout 128. Safety lockout 128 defines a slot 160 dimensioned to slidably receive the knife 40. In the retracted position of the knife 40, the leading edge 40a of knife 40 is confined within slot 160 safety lockout 128 to prevent accidental engagement and injury to medical personnel with leading edge 40a of knife 40.

Referring again to FIGS. 2-3, anvil half-section 12 includes a proximal handle portion 12a and a distal anvil portion 12b. Anvil portion 12b includes a staple deforming portion 198 which, as known in the art, includes a plurality of staple deforming recesses and faces a top surface of SULU 18 when SULU 18 is positioned in the channel member 22. As is also known in the art, the staple deforming portion 198 includes a central longitudinal slot (not shown) for receiving the knife 40 (FIG. 17) as the knife 40 is moved through the SULU 18. The staple deforming portion 198 can be formed integrally with anvil half-section 12, or in the alternative, secured to anvil half-section 12 by a fastening process such as welding. A pair of locating fingers 170 (FIG. 3) are positioned adjacent the proximal end of the staple deforming portion 198 of anvil portion 12b. Locating fingers 170 are received in grooves in SULU 18 to properly align SULU 18 with staple determining portion 198 when the apparatus is in a clamped position.

Figure 28:
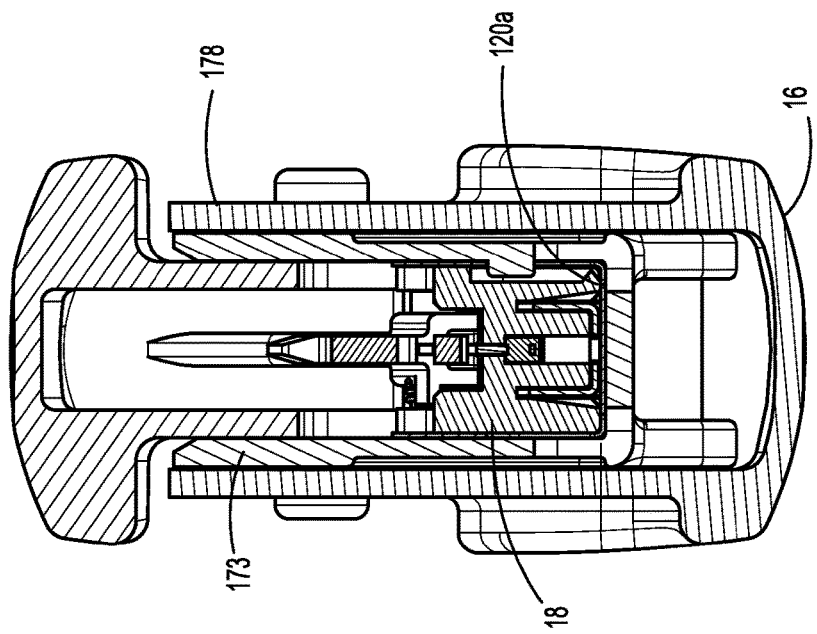
FIG. 28 is a cross-sectional view taken along section lines 28-28 of FIG. 26.

A central portion of anvil half-section 12 includes a pair of cylindrical lateral support members 172. During assembly of anvil half-section 12 and cartridge receiving half-section 14, lateral support members 172 are supported in U-shaped recesses 174 defined in a central portion 173 of cartridge receiving half-section 14 (FIG. 28). A distal wall 173a of central portion 173 defines a tissue stop (FIG. 3). Lateral support members 172 are also positioned to be received in cutouts 176 formed on spaced flange portions 178 of clamping lever 16 when the clamping lever 16 is moved to the clamped position (FIG. 2B). Proximal handle portion 12a is ergonomically formed and includes a thumb-engaging abutment 180 and a gripping portion 182. A proximal end of handle portion 12a includes a downwardly extending finger 184 which includes a pair of opposed teardrop shaped protrusions 186 which will be discussed in further detail below. Alternately, protrusions 186 may assume a variety of configurations.

Cartridge receiving half-section 14 includes spaced centrally disposed U-shaped recesses 174 positioned to support lateral support members 172 of anvil half-section 12. The proximal end of cartridge receiving half-section 14 includes a pair of vertical support members 188. Each vertical support member 188 includes an elongated vertical slot 188a having a rounded bottom surface. Vertical slots 188a are dimensioned to receive protrusions 186 formed on finger 184 of anvil half-section 12 (FIG. 21) when the anvil half-section 12 is supported on the cartridge receiving half-section 14 during assembly. By positioning protrusion 186 within the vertical slots 188a, anvil half-section 12 can be pivoted in a scissor-like manner with respect to the cartridge receiving half-section 14 between open and closed positions. In one embodiment, protrusions 186 have a teardrop profile. At least one sidewall of cartridge receiving half-section 14 includes a depression 189 (see FIG. 3) which will be discussed in further detail below.

Clamping lever 16 also includes a handle portion 190 including a grip 190a and a thumb engaging abutment 192. As discussed above, a pair of spaced flange portions 178 is supported on the distal end of clamping lever 16. Each flange portion 178 defines a cutout 176 dimensioned to receive a respective lateral support member 172 of anvil half-section 12 when stapler 10 is moved towards clamped position (FIG. 2B). The distal end of clamping lever 16 also defines a pair of openings 194 which are dimensioned to receive a pivot member 187. Pivot member 187 is dimensioned to extend through openings 195 in cartridge receiving half-section 14 and openings 194 in clamp lever 16 to pivotally secure clamp lever 16 to cartridge receiving half-section 14.

Figure 2A:
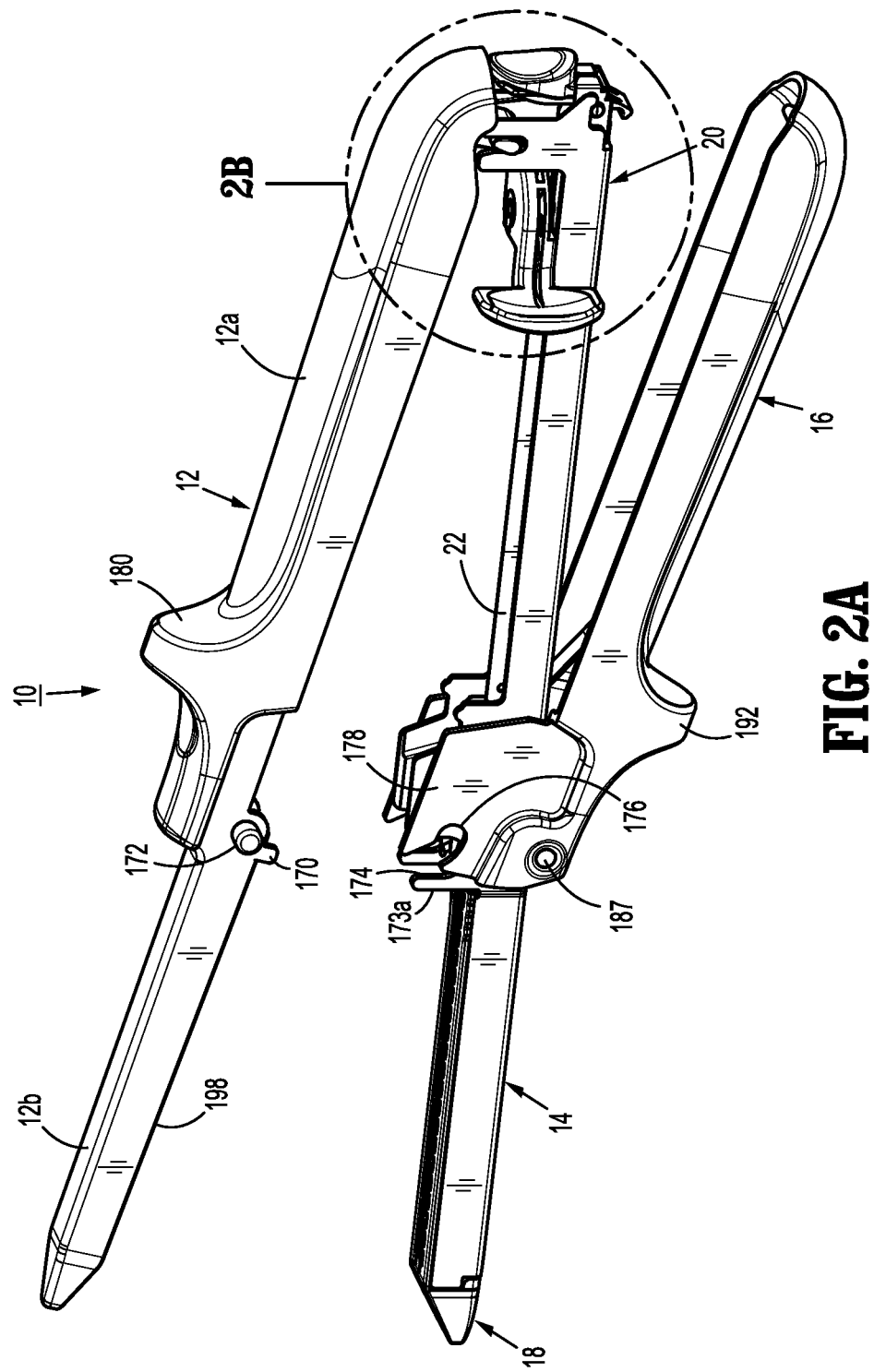
FIG. 2A is a side perspective view of the surgical fastener applying apparatus shown in FIG. 1 in the open position.
Figure 3A:
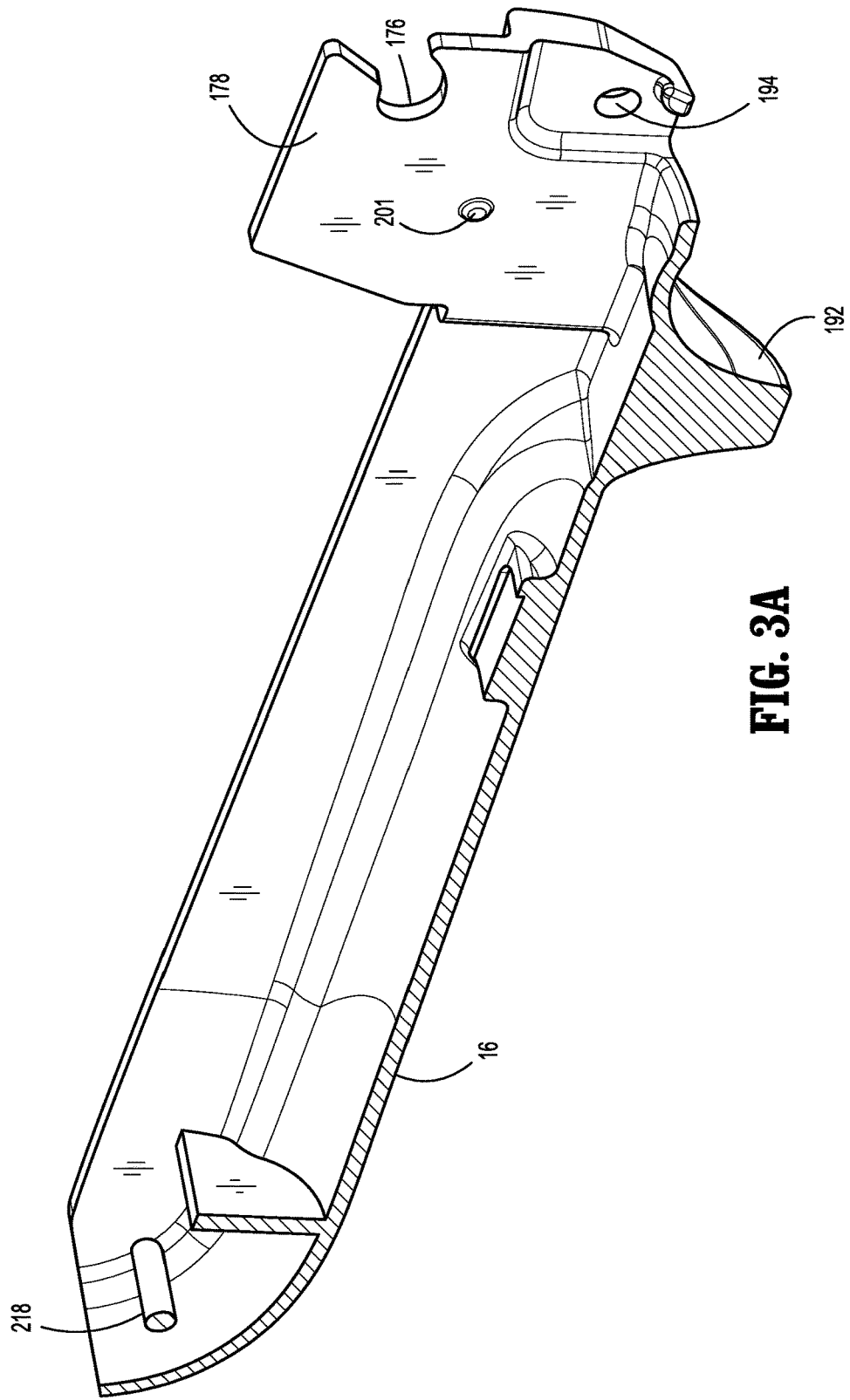
FIG. 3A is a side cross-sectional view of the clamp lever of the fastener applying apparatus shown in FIG. 1.
Figure 7:
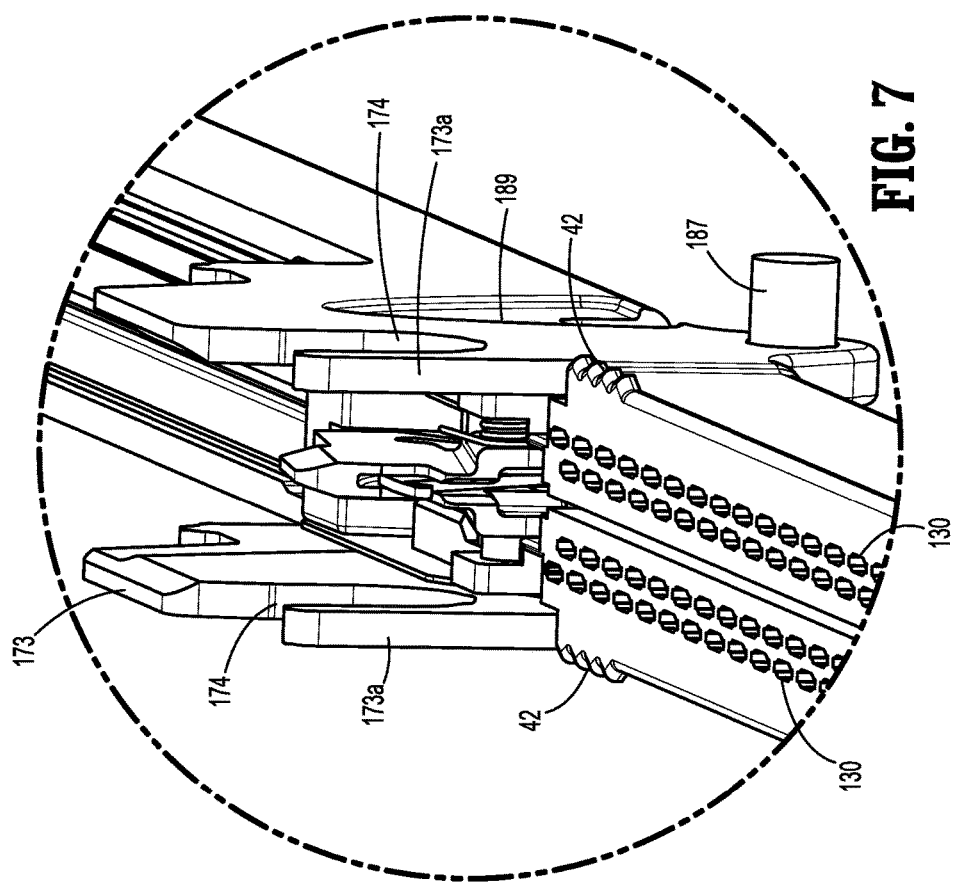
FIG. 7 is an enlarged view of the indicated area of detail shown in FIG. 6.
Figure 6:
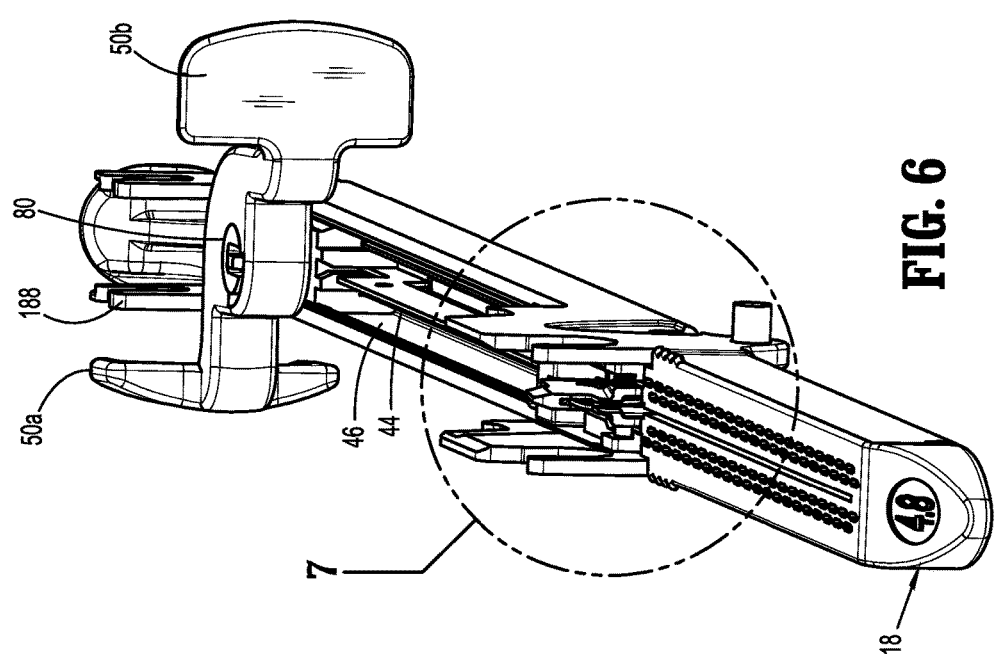
FIG. 6 is a perspective view from above of the cartridge receiving half-section of the surgical fastener applying apparatus with the SULU and the firing assembly supported therein.

As shown in FIG. 3A, an inner wall of clamping lever 16 includes a protrusion 201. Protrusion 201 is positioned within depression 189 (FIG. 2A) formed in the sidewall of cartridge receiving half-section 14 to releasably retain clamp lever 16 in the unclamped position or open position (FIG. 2A).

In order to load firing assembly 20 into proximal portion 24b of channel member 22, the stationary housing 26 of firing assembly 20 is slid into the channel member 22 through the proximal end of channel member 22 until pivot members 29 are received in recesses 30 formed in the proximal end of channel member 22. After firing assembly 20 is loaded, the SULU 18 can be loaded into distal portion 24a in the manner discussed above.

Referring to FIGS. 2 and 2B, after SULU 18 and firing assembly 20 are loaded into channel member 22, anvil section 12 can be assembled to cartridge receiving half-section 14. To attach anvil half-section 12 to cartridge receiving half-section 14, protrusions 186 of fingers 184 are positioned in vertical slots 188a of vertical support member 188 of cartridge receiving half-section 14. Thereafter, anvil half-section 12 is rotated towards cartridge receiving half-section 14 to position lateral supports members 172 in U-shaped recesses 174.

Figure 2B:
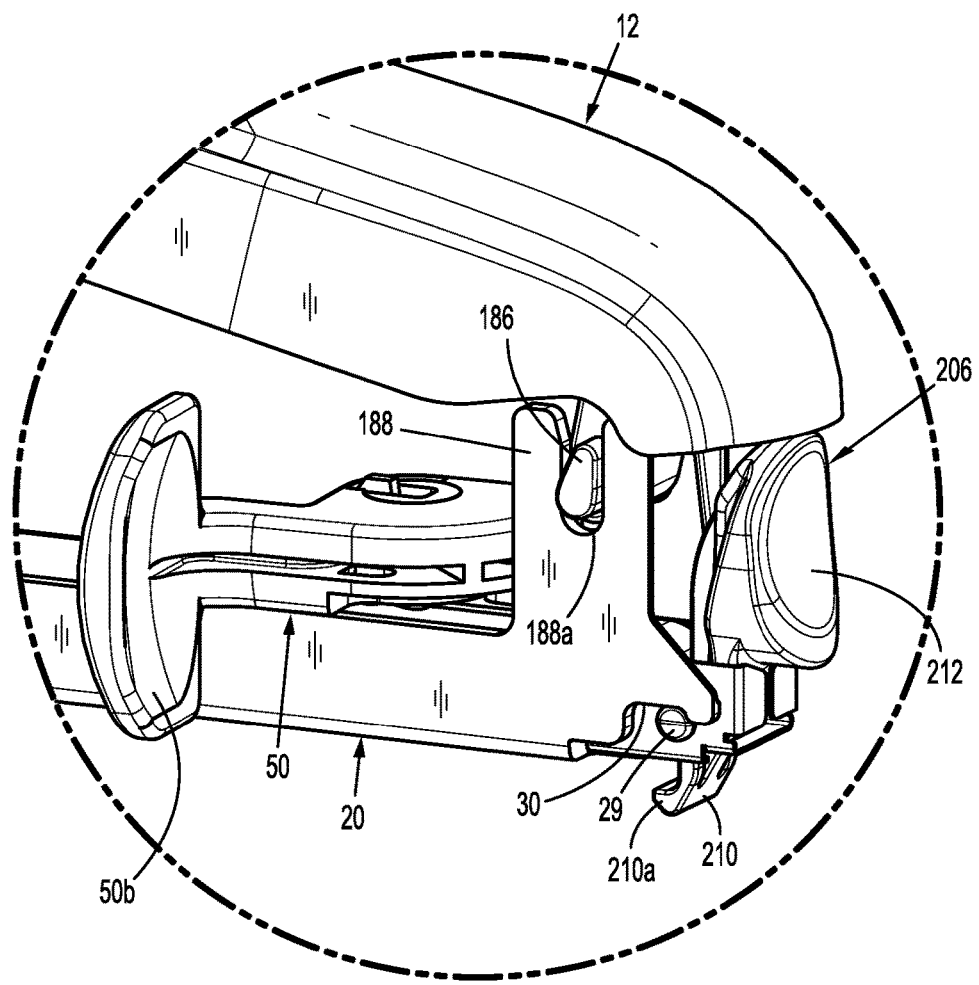
FIG. 2B is an enlarged view of the indicated areas of detail shown in FIG. 2A.

In order to position surgical stapler 10 in the clamped position, clamping lever 16 is rotated in a counter-clockwise direction from the position shown in FIG. 2A. As clamping lever 16 is rotated, lateral support members 172 are received in cutouts 176 (FIG. 2) of flange portions 178 and cammed towards cartridge receiving half-section 14. As shown in FIG. 3, a spring member 200 is secured to an inner surface of clamping lever 16, such as by welding, at a position to engage cartridge receiving portion 14 to urge clamping lever 16 to the non-clamped position shown in FIG. 2A. In the clamped position shown in FIG. 1, the staple deforming portion 198 is positioned in close approximation with the top surface of SULU 18.

Figure 21:
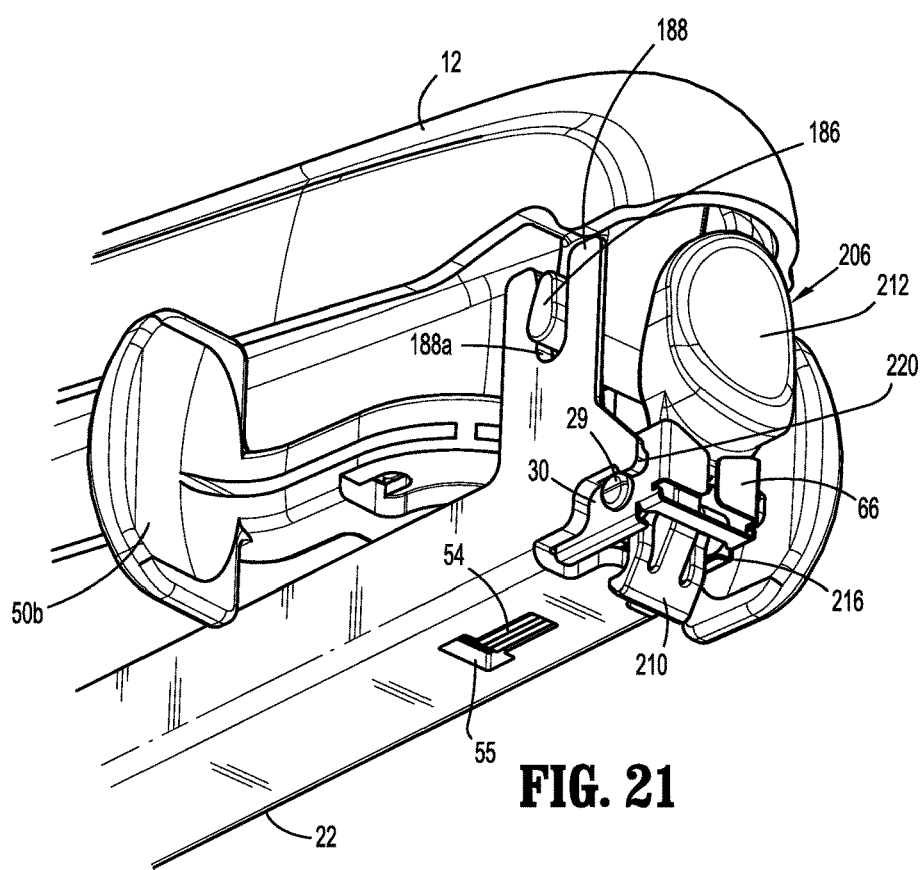
FIG. 21 is a perspective view of the proximal end of the surgical fastener applying apparatus shown in FIG. 18 in the open position.
Figure 22:
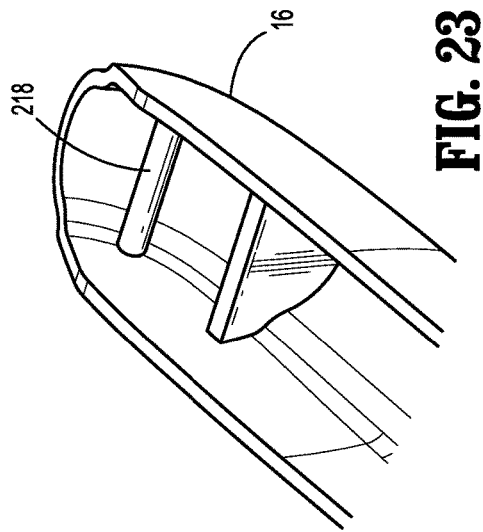
FIG. 22 is an enlarged view of the indicated area of detail shown in FIG. 18.
Figure 23:
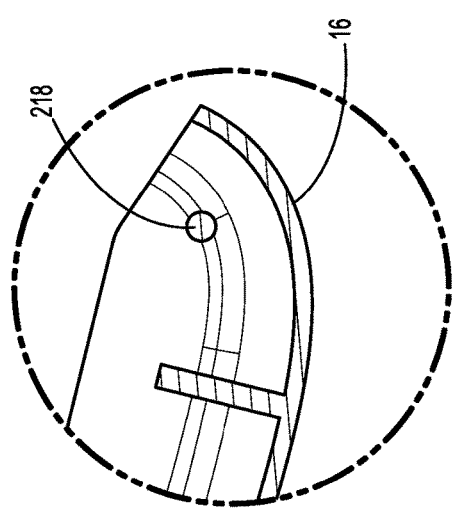
FIG. 23 is a perspective view from below of the proximal end of the clamping lever of the surgical fastener applying apparatus shown in FIG. 1.
Figure 24:
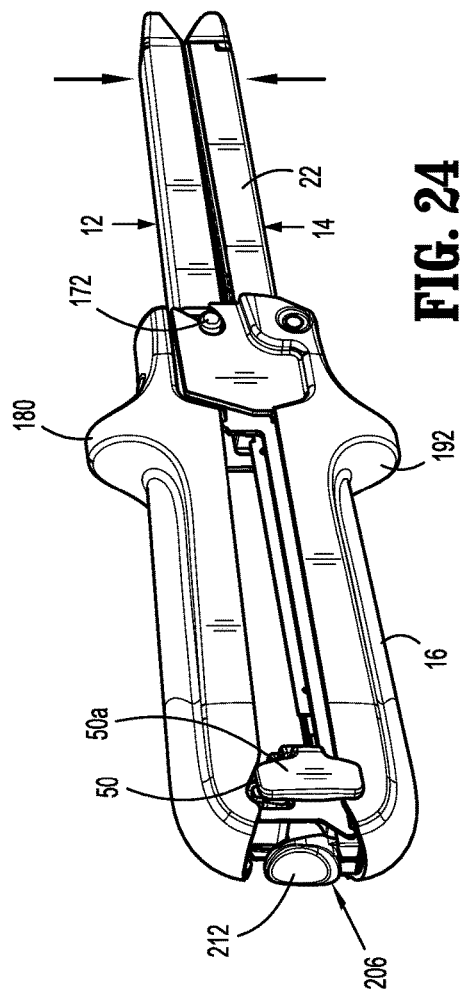
FIG. 24 is a side perspective view of the surgical fastener applying apparatus shown in FIG. 1 in the clamped position.
Figure 25:
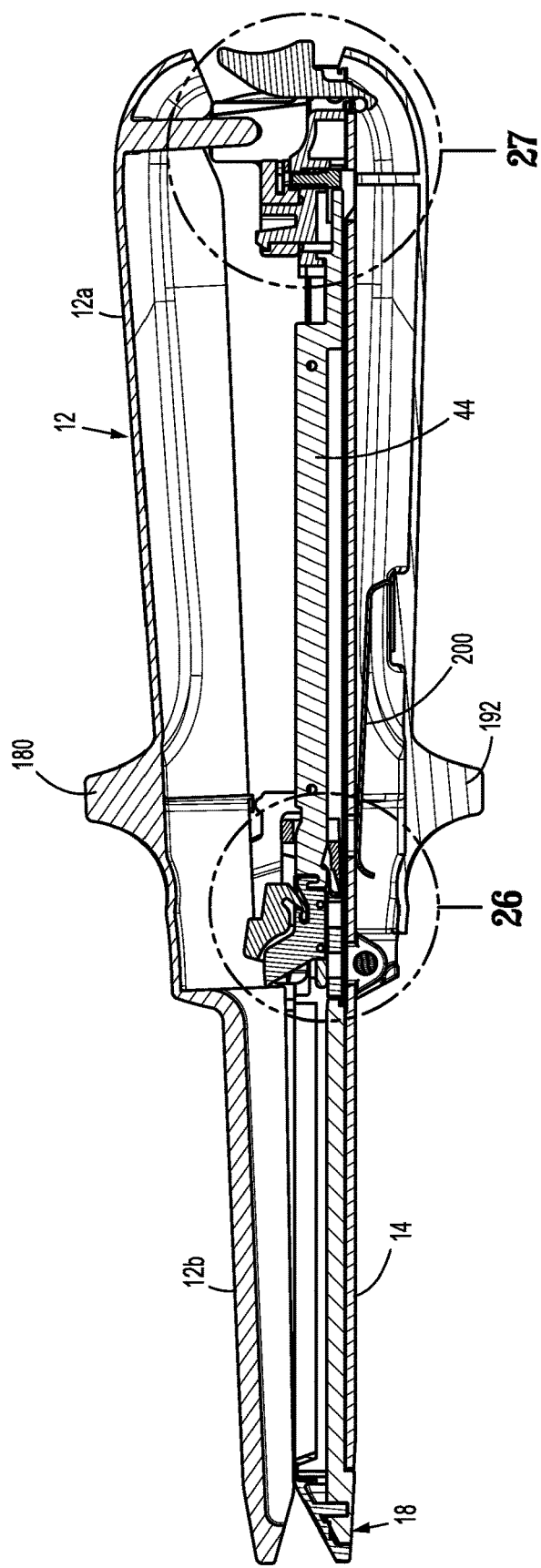
FIG. 25 is a side cross-sectional view of the surgical fastener applying apparatus shown in FIG. 24 in the clamped position.

Referring to FIGS. 3, 3A and 12, as discussed above, a pivotal locking member 206 is pivotally supported on the proximal end of stationary housing 26 of firing assembly 20. Pivotal locking member 206 includes pivot members 29 which extend through openings 28 defined in stationary housing 26. A finger engagement member 212 is positioned on one end of locking member 206 and a latch portion 210 is positioned on the other end of locking member 206. Latch portion 206 includes a hook member 210a. A biasing member 214 is positioned about a pivot member 29 to urge latch portion 210 inwardly towards stationary housing 26 of firing assembly 20. When locking member 206 is secured on firing assembly 26, latch portion 210 extends downwardly through an opening 216 in a proximal end of stationary housing 26 to a position below a bottom surface of channel member 22 (FIG. 20). As discussed above, the ends of pivot members 29 are received in cutouts 30 formed in the proximal end of cartridge receiving half-section 14 to releasably secure firing assembly 20 within proximal channel portion 24b of channel member 22 (FIG. 21). Cutouts 30 are partially defined by downturned fingers 220 to retain firing assembly 26 within channel member 22 (FIG. 3).

Referring to FIG. 3A, a proximal end of clamping lever 16 includes an engagement member, e.g., cylindrical post 218, which is positioned to be engaged by hook member 210a of latch portion 210 when the clamp lever 16 is moved to the clamped position (FIG. 27). Although a post is illustrated, other engagement member configurations are envisioned. As can be seen by viewing FIG. 27, as clamping lever 16 is moved towards the clamped position, an angled face 222 of latch portion 210 engages post 218. This engagement causes locking member 206 to pivot about pivot members 29 such that hook member 210a of latch portion 210 passes by and then snaps into engagement with post 218. To release latch portion 210 from post 218, engagement member 212 of locking member 206 is depressed to pivot latch portion 210 out of engagement with post 218. When this occurs, spring member 200 urges clamping lever 16 to the unclamped position.

Figure 26:
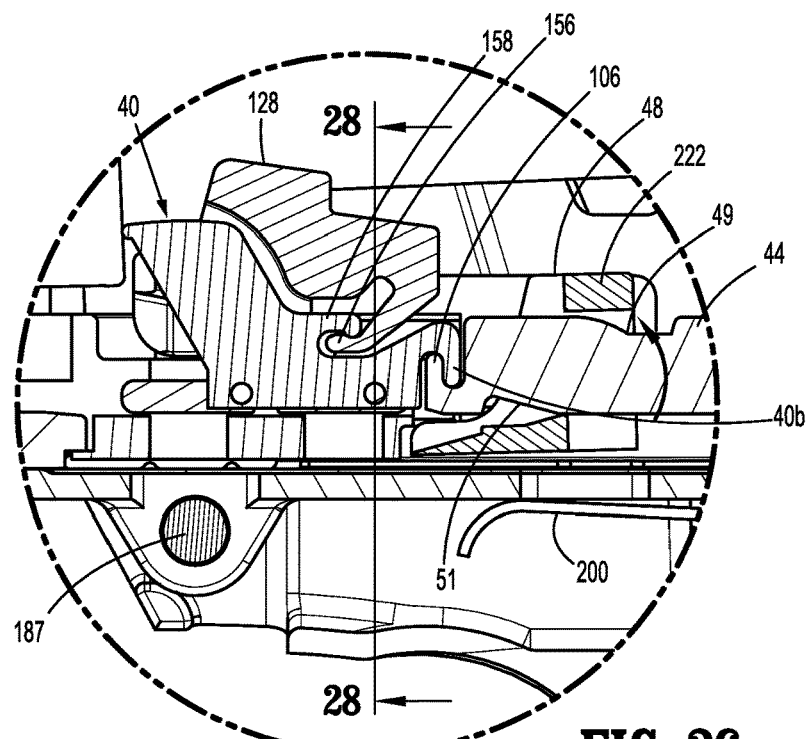
FIG. 26 is an enlarged view of the indicated area of detail shown in FIG. 25.

Referring to FIGS. 3, 12, 19 and 26, as discussed above, guide block 48 is pivotally supported in stationary housing 26 of firing assembly 20. Guide block 48 includes a distally extending nose portion 220 (FIGS. 12 and 26) which rests beneath SULU 18 when SULU 18 is supported in channel member 22. The internal surface of guide block 48 includes locking surfaces 222 (FIG. 19) which are received in notches 49 and 51 of knife actuating bar 44 when the stapler 10 is in an unclamped position. When the SULU 18 is positioned in the channel member 22, prior to moving clamp lever 16 to the clamped position, SULU 18 is positioned atop nose portion 220 and is not fully seated in the channel member 22, as discussed above. When the stapler 10 is moved to the clamped position, locating fingers 170 (FIG. 3) engage a top surface of body 120 of SULU 18 to fully seat SULU 18 in channel member 22. As discussed above, locating fingers 170 are received in grooves in SULU 18 to properly position SULU 18 in relation to anvil portion 12b. As SULU 18 is fully seated in channel member 22, SULU 18 presses downwardly on nose portion 220 of guide block 48 to pivot guide block 48 about protrusions 72. When guide block 48 pivots, locking surfaces 222 move from notches 49 and 51 to unlock knife actuating bar 44 (FIG. 26). This configuration prevents movement of the knife actuating bar 44 in relation to guide block 48 prior to clamping to ensure that the knife actuating bar 44 and SULU knife 40 remain properly positioned for operational engagement prior to use.

Referring to FIGS. 24-28, when stapler 10 is in the clamped, unfired position, slide block 52 of firing assembly 20 is in the retracted position at the proximal end of channel member 22 and stationary housing 26. See FIG. 27. In this position, pedal 54 is positioned in cutout 55 of channel member 22 and pin 88 of pedal 54 is positioned in arcuate recess 94 of firing lever 50 beneath stop recesses 94a. As such, firing lever 50 can be pivoted to facilitate actuation of stapler 10 from either side of the stapler 10. In addition, in this position of slide block 52, finger 108 of knife actuating bar 44 is positioned adjacent the distal wall of recess 110 of slide block 52. Latch portion 210 of locking member 206 is also engaged with post 218 to retain clamping lever 16 in the clamped position.

Referring to FIG. 26, when slide block 52 is in the refracted position, knife 40 and cam surfaces 114b of cam bar 46 are positioned in the proximal end of SULU 18 and, proximal hook 156 of safety lockout 128 is positioned in engagement with engagement member 158 of knife 40 to retain safety lockout 128 in the locked orientation. In addition, downturned hook portion 40b of knife 40 is engaged with upturned hook portion 106 of knife actuating bar 44 to connect firing assembly 20 to knife 40 of SULU 18.

Figure 29:
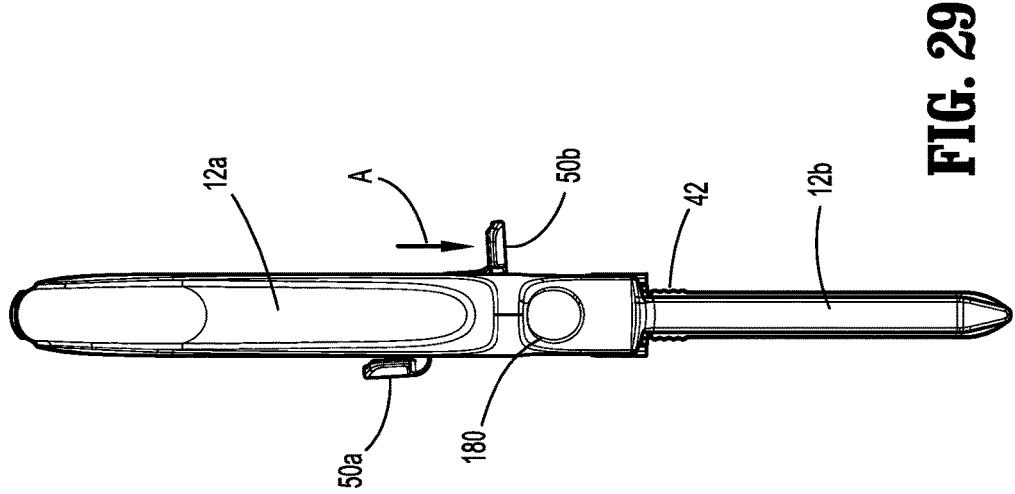
FIG. 29 is a top view of the surgical fastener applying apparatus shown in FIG. 1 as the firing assembly is moved through an actuating stroke to eject fasteners from the fastener applying apparatus.

Referring to FIGS. 29-32, when the firing lever 50 is advanced distally in the direction indicated by arrow "A" in FIG. 29, slide block 52 is moved distally within stationary housing 26 of firing assembly 20 to effect corresponding movement of cam bar 46 and delayed movement of knife actuating bar 44. As discussed above, the delayed movement of the knife actuating bar 44 is equal to the length of recess 110 of slide block 52 and results from movement of finger 108 of knife actuating bar 44 within recess 110 of slide block 52. Movement of knife actuating bar 44 with slide block 52 begins when finger 108 abuts the proximal wall 112 of recess 110. As cam bar 46 is moved distally through stationary housing 26 of firing assembly 20, cam surfaces 114b on sidewalls 114 of cam bar 46 are advanced through SULU 18 to sequentially engage pushers 122 to eject staples 126 from slots 130 of body 120. Concurrently, since the distal end of knife actuating bar 44 is engaged with knife 40, knife 40, after the preset delay, is advanced through SULU 18 to incise tissue between the staple lines.

Figure 32:
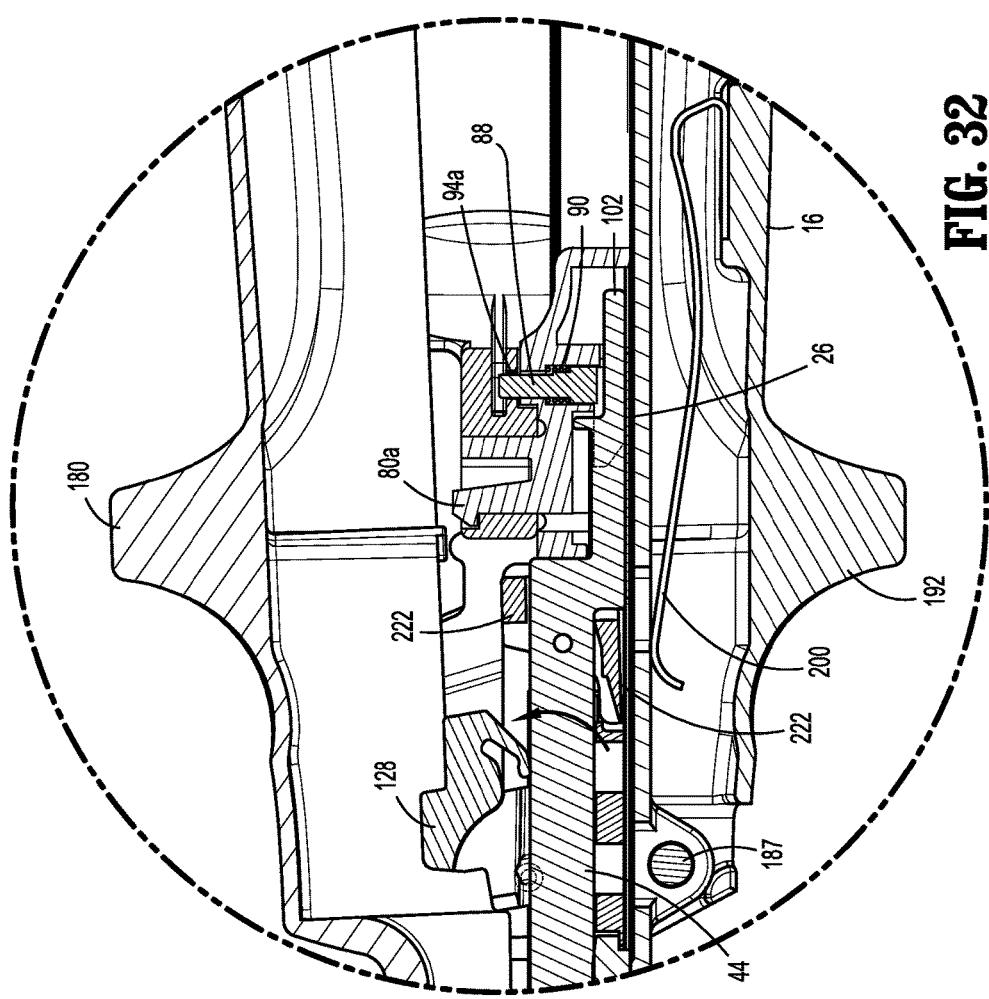
FIG. 32 is an enlarged view of the indicated are of detail shown in FIG. 30.

As shown in phantom in FIG. 32, when slide block 52 moves distally within stationary housing 26, pedal 54 rides up over channel member 22 and moves along inner surface of stationary housing 26 of firing assembly 20. When this occurs, pin 88 of pedal 54 moves into a stop recess 94a to prevent further pivotal movement of firing lever 50.

Figure 31:
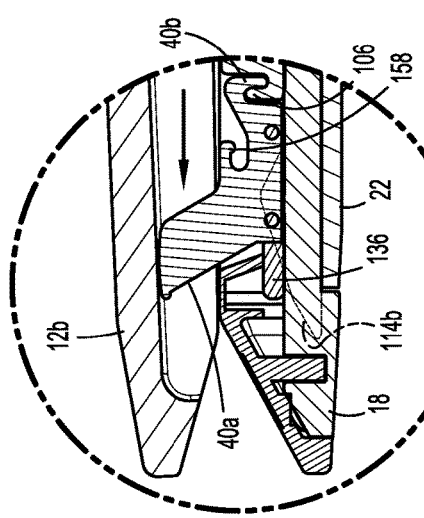
FIG. 31 is an enlarged view of the indicated area of detail shown in FIG. 30.

Referring to FIGS. 31 and 32, when knife 40 is moved distally within SULU 18, engagement member 158 of knife 40 is disengaged with proximal hook 156 of safety lockout 128.

Referring to FIGS. 33 and 34, when the firing lever 50 is returned to its proximal-most position to retract cam bar 46 and knife 40, and the locking member 206 is depressed to disengage latch portion 210 from post 218, spring 200 urges clamping lever 16 to its unclamped position to allow stapler 10 to move to the open position. In the open position, anvil half-section 12 is spaced from cartridge receiving half-section 14 and spring 152 (FIG. 17) pivots safety lockout 128 in the direction indicated by arrow B in FIG. 34 about pivot member 150 to its unlocked position such that safety lockout 128 projects upwardly from SULU 18. In the unlocked position, safety lockout 128 prevents movement of the stapler 10 back to the clamped position. In order to reuse stapler 10, used SULU 18 must be replaced with a new SULU 18.

During a surgical procedure, SULU 18 can be replaced multiple times to facilitate multiple uses of stapler 10 on a single patient. Since each SULU 18 is provided with a fresh knife 40, tearing of tissue is minimized. After the surgical procedure, the used SULU(S) 18 and the firing assembly 20 can be removed from the channel member 22 and disposed of in an appropriate manner. The anvil half-section 12, cartridge receiving half-section 14 and clamping lever 16 can now be sterilized, such as by autoclaving, and reused with a sterilized SULU 18 and firing assembly 20 in the manner discussed above. Because the locking member 206 forms part of the firing assembly 20 and is disposable, fewer areas remain on the reusable components for tissue and fluids to become trapped. As such, the reusable components of the apparatus can be more easily sterilized.

In the surgical stapler described above, the SULU 18 and the firing assembly 20 are independently secured to and independently removed from the channel member 22 of the cartridge receiving half-section 14. In alternative embodiments illustrated in FIGS. 35-36B, the SULU 18 and the firing assembly 20 are configured to form a single disposable unit, and the cartridge receiving half-section is configured to receive the single disposable unit. In particular, the stationary housing of the firing assembly is configured to support both the SULU and the firing components of the surgical stapler 10, e.g., knife actuating bar, cam bar, guide block, and slide block shown in FIGS. 8-12. When the stationary housing is inserted into the channel member 22 of the cartridge receiving half-section, the SULU and the firing components are concurrently mounted to the cartridge receiving half-section. The stationary housing includes a lockout structure to prevent insertion of the SULU into the stationary housing after the stationary housing has been inserted into the cartridge receiving half-section. Thus, in these embodiments, the SULU must be inserted into the stationary housing before inserting the stationary housing into the cartridge receiving half-section. Specific embodiments of the stationary housing are discussed below.

Figure 35:
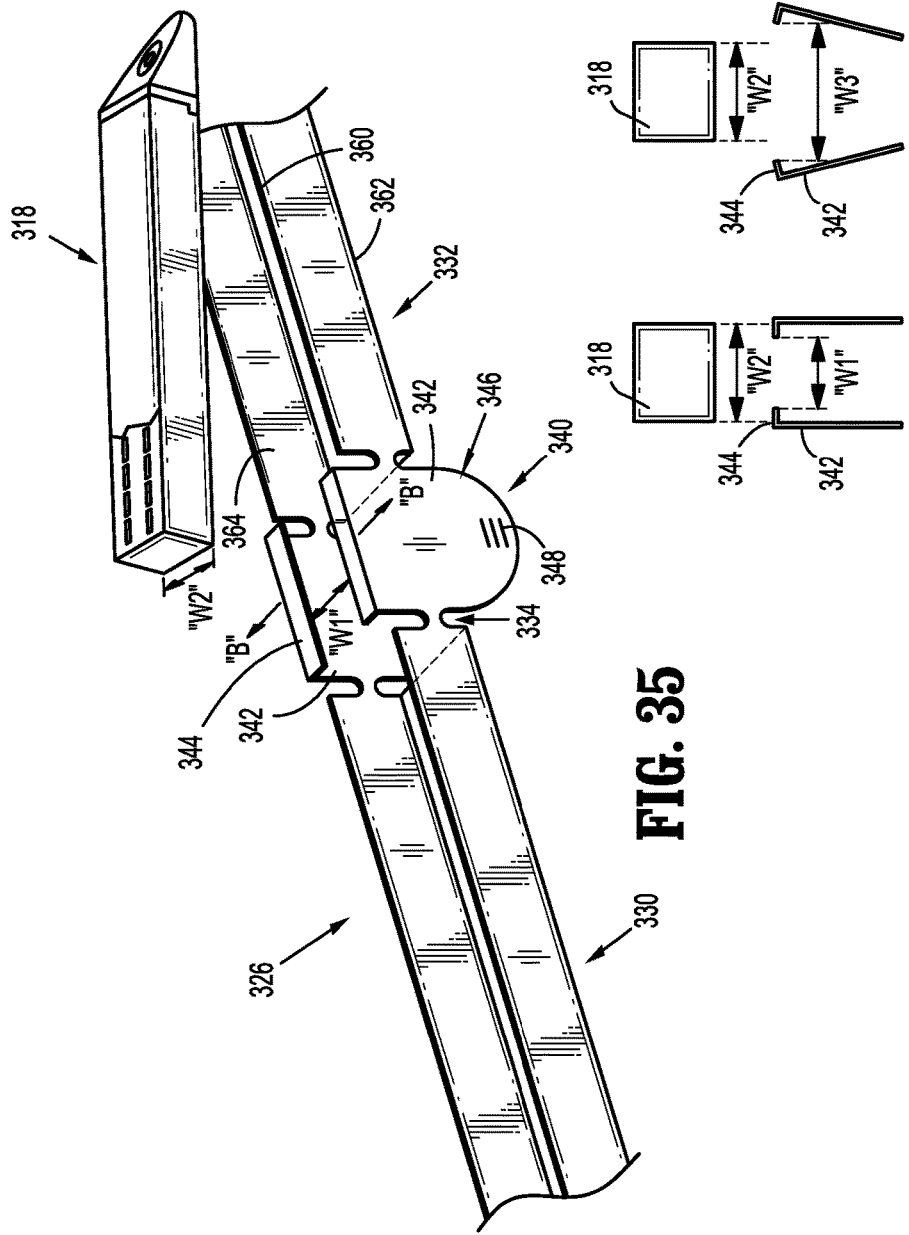
FIG. 35 is a perspective view of an alternate embodiment of the stationary housing of the firing assembly prior to insertion of the SULU.

FIG. 35 schematically illustrates an alternate embodiment of the stationary housing 326 associated with the firing assembly 320. The stationary housing 326 can define a length substantially similar to that of the cartridge receiving half-section 14 (FIG. 3). The stationary housing 326 is configured to be releasably received within the channel member 22 (see also FIG. 3) of the cartridge receiving half-section 14. The stationary housing 326 includes a proximal portion 330, a distal portion 332 and a center portion 340 therebetween.

The proximal portion 330 of the stationary housing 326 is configured to support the firing components of the surgical stapler 10 shown in FIGS. 8-12 in the same manner as stationary housing 26, such firing components including the knife actuating bar, cam bar, guide block, and slide block (not shown in FIG. 35).

The distal portion 332 and the center portion 340 of the stationary housing 326 together are of a length substantially similar to that of the SULU (single use loading unit) 318, and together are configured to releasably receive the SULU 318. The stationary housing 326 has a first position which prevents full operable insertion of the SULU 318 into the distal portion 332 and the center portion 340 of the stationary housing 326, and a second position which permits full operable insertion of the SULU 318 into the distal portion 332 and the center portion 340 of the stationary housing 326.

The distal portion 332 of the stationary housing 326 has a U-shaped frame 360 including a bottom wall 362 and a pair of sidewalls 364. The proximal portion 330 may have an identical or similar structure as that of the distal portion 332. The center portion 340, on the other hand, does not have a bottom wall, but rather has a pair of sidewalls 342 that are hingedly attached to the proximal portion 330 and the distal portion 332 via live hinges 334, which are flexible and resilient. Each sidewall 342 of the center portion 340 is pivotable about the live hinges 334.

As illustrated in FIGS. 35-35A, when the stationary housing 326 is in the first position, the sidewalls 342 of the center portion 340 are correspondingly in their first, unbiased position in which the sidewalls 342 are in substantially parallel relation with respect to each other, and the sidewalls 342 are substantially aligned with respect to the sidewalls 364 of the distal portion 332. By contrast, when the stationary housing 326 is in the second position, the sidewalls 342 of the center portion 340 are correspondingly in their second, inclined position as shown in FIG. 35B in which the sidewalls 342 are inclined away from each other. In the absence of any external force or pressure, the sidewalls 342 naturally assume their first position, and for the same reason, the stationary housing 326 naturally assumes its first position. Application of force pivots or flexes the sidewalls 342 about the live hinges 334 due to the flexible nature of the live hinges 334, moving the sidewalls 342 from the first position to the second, inclined position, correspondingly moving the stationary housing 326 from its first position to its second position. Upon removal of the force, the sidewalls 342 resume their first position owing to the resilient nature of the live hinges 334, and simultaneously returning the stationary housing 326 to its first position.

It is also contemplated in an alternate embodiment that the sidewalls are formed such that they require manual application of force to pivot between both first and second positions. Alternatively, the sidewalls 342 can be biased to the non-blocking position with the sidewalls of the cartridge receiving half sections moving sidewalls 342 to the blocking position.

Each sidewall 342 includes a downwardly extending portion 346 which can extend beyond the bottom surface 362 of the distal portion 332, and serves as a manual member to facilitate manual manipulation of the sidewalls 342. In one embodiment, the downwardly extending portions 346 each have a semi-circular configuration. Alternatively, other configurations are contemplated. An inward pressure upon the pair of downwardly extending portions 346 toward the longitudinal axis of the stationary housing 326, e.g. by the user's fingers, effects pivotal movement of the sidewalls 342 from the first, unbiased position to the second, inclined position. The sidewalls 342 return back to the first, unbiased position upon release of the inward pressure. The downwardly extending portions 346 may further include a plurality of ridges 348 protruding outwardly therefrom to facilitate frictional engagement between the user's fingers and the downwardly extending portions 346 during manual manipulation.

Each sidewall 342 has a top flange 344 extending radially inwardly from the top thereof, defining an opening (gap) therebetween. When the sidewalls 342 of the center portion 340 are in their first position as illustrated in FIG. 35A, the two top flanges 344 are in a substantially coplanar configuration, and define a lateral dimension or opening "W1" therebetween which is less than the lateral dimension "W2" of the SULU 318, thereby preventing entry of the SULU 318 into the stationary housing 326. When the sidewalls 342 of the center portion 340 are moved to their second, inclined position as illustrated in FIG. 35B, by inward pressure on portions 346, the two flanges 344 move apart in the direction as indicated by "B" in FIG. 35B creating an enlarged lateral dimension "W3" which is greater than the lateral dimension or opening (gap) "W2" of the SULU 318, thereby allowing entry of the SULU 318 into the stationary housing 326.

Accordingly, when the sidewalls 342 are in their first position, the top flanges 344 prevent full insertion of the SULU 318 to an operable position in the stationary housing 326. When the sidewalls 342 are in their second, inclined position, the top flanges 344 are spaced apart to permit full insertion of the SULU 318 into the stationary housing 326 to an operable position cooperating with the pusher assembly so the staples contained in the SULU 318 can be fired. After the SULU 318 is positioned into the stationary housing 326, pressure on portions 346 is released, enabling the sidewalls 342 to return to their first position to prevent removal of the SULU 318 from the stationary housing 326. When the SULU 318 is securely held within the stationary housing 326, the stationary housing 326 simultaneously supports the SULU 318 as well as the firing components of the surgical stapler 10. As a result, the stationary housing 326, the SULU 138, and the firing components of the surgical stapler 10 together form a single disposable unit.

During operation, a user first squeezes the downwardly extending portions 346 of the stationary housing 326 towards each other to adjust the sidewalls 342 of the center portion 340 to their second, inclined position, moving the stationary housing 326 to its second position to readily accept a SULU 318 therein. Next, the user positions the SULU 318 within the center portion 340 and the distal portion 332 of the stationary housing 326. After the SULU 318 is successfully positioned within the stationary housing 326, the user releases the semi-circular portions 346, causing the sidewalls 342 to return to their first normal position, and simultaneously moving the stationary housing 326 to its first position. Once the stationary housing 326 resumes its first position, the stationary housing 326 securely holds the SULU 318 therein. With the firing components already loaded in the proximal portion 330 of the stationary housing 326, thereby forming a pusher assembly, and the SULU 318 loaded in the center portion 340 and the distal portion 332 of the stationary housing 326, the firing components, the SULU 318 and the stationary housing 326 together form a single disposable loading unit. The user then mounts the single disposable unit into the cartridge receiving half-section by placing the stationary housing 326 into the channel member of the cartridge receiving half-section.

If the user mounts the stationary housing 326 into the cartridge receiving half-section without first inserting the SULU 318 into the stationary housing 326, the walls of the cartridge receiving half-section confines the sidewalls 342 of the center portion 340 to their first position, thereby forming a locking or blocking structure preventing or blocking subsequent entry of the SULU 318 into the stationary housing 326. That is, the sidewalls 342 do not have sufficient space to be inclined to widen the opening therebetween as there movement is obstructed. In that case, the stationary housing 326 must be removed from the cartridge receiving half-section to then incline the sidewalls 342 to allow the SULU 318 to be positioned in the stationary housing 326. Consequently, the SULU 318 needs to be inserted into the stationary housing 326 prior to insertion of the stationary housing 326 into the stapler.

Figure 36:
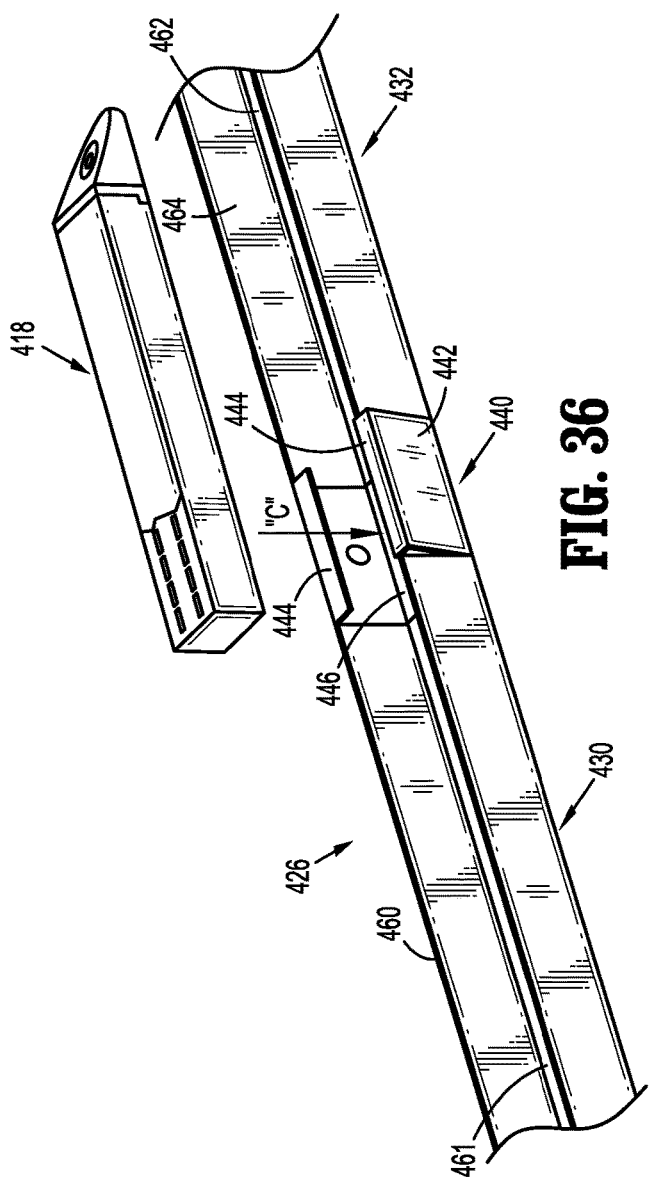
FIG. 36 is a schematic view of another alternate embodiment of the stationary housing of the firing assembly prior to insertion of the SULU therein.
Figure 36B:
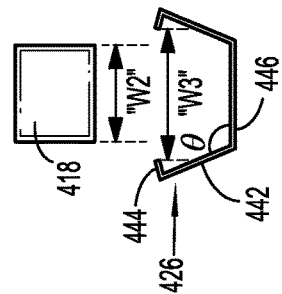
FIG. 36B is a side cross-sectional view of a center portion of the stationary housing of FIG. 36 shown in a position that allows entry of the SULU therein.

FIGS. 36-36B illustrate another alternate embodiment of the stationary housing 426 of firming assembly 420. The stationary housing 426 includes a proximal portion 430, a distal portion 432 and a center portion 440 therebetween. The proximal portion 430 and the distal portion 432 have structures and functions similar to that of the proximal and distal portions 330, 332, of stationary housing 326, respectively, as described above.

The center portion 440 defines a U-shaped configuration, including a pair of sidewalls 442, a pair of flanges 444 each extending substantially perpendicular from its associated sidewall 442 (toward a longitudinal axis of the stationary housing 426), and a bottom surface 446. The bottom surface 446 is permanently attached to or alternatively integrally formed with the bottom surface 462 of the distal portion 432 and the bottom surface 461 of the proximal portion 430. Each sidewall 442 is hingedly attached to the bottom surface 446, and pivotable with respect to the bottom surface 446.

Figure 36A:
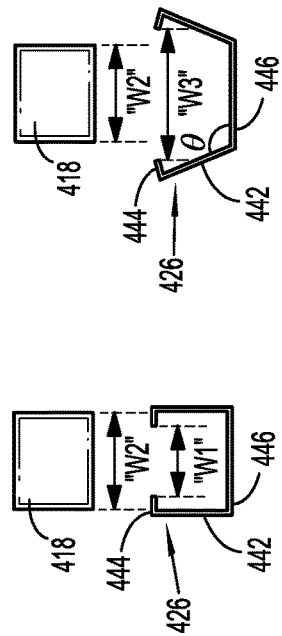
FIG. 36A is a side cross-sectional view of a center portion of the stationary housing of FIG. 36 shown in a position that prevents entry of the SULU therein.

Similar to the stationary housing 326, the stationary housing 426 also has a first position illustrated in FIG. 36A which prevents or blocks entry of the SULU 418 therein, and a second position illustrated in FIG. 36B which permits entry of the SULU 418 therein. In some embodiments, the first position can be the normal biased position.

When the stationary housing 426 is in its first position illustrated in FIG. 36A, the pair of sidewalls 442 is correspondingly in a first position in which each sidewall 442 is substantially perpendicular to the bottom surface 446, and the top flanges 444 are substantially coplanar with respect to each other and define a lateral dimension or opening (gap) "W1" smaller than the lateral dimension "W2" of the SULU 418, thereby forming a lockout structure preventing insertion of the SULU 418 into the stationary housing 426.

When the stationary housing 426 is in its second position illustrated in FIG. 36B, the pair of sidewalls 442 is correspondingly in a second position in which the sidewalls 442 are inclined away from each other. Each sidewall 442 now defines an obtuse angle, e.g. "θ", with respect to the bottom surface 446. In this position, the top flanges 444 have a lateral dimension "W3" therebetween, which is greater than the lateral dimension or opening (gap) "W2" of the SULU 418, thereby permitting entry of the SULU 418 into the stationary housing 426 into an operable position to cooperate with the pusher assembly so the staples contained in the SULU 418 can be fired. Note SULU 418 (and SULU 318) can be identical to SULU 18.

During operation, the user may first pivot each sidewall 442 outwardly to adjust them to the second position as shown in FIG. 36B. The user then places the SULU 418 into the center portion 440 and the distal portion 432 of the stationary housing 462. Next, the user releases (or pivots the sidewalls back to the first position in embodiments where the sidewalls are not biased to the first position) each sidewall 442 to enable it to return inwardly to the first position as shown in FIG. 36A, securing the SULU 418 within the stationary housing 426. At that time, the SULU 418, the stationary housing 426, and the firing components carried by the stationary housing 426 together form a single disposable unit. The user then mounts the single disposable unit into the cartridge receiving half-section 14 (FIG. 3) by placing the stationary housing 426 into the channel member (FIG. 3) of the cartridge receiving half-section 14. If the user mounts the stationary housing 426 into the cartridge receiving half-section without first inserting the SULU 418 into the stationary housing 426, the cartridge receiving half-section would confine the sidewalls 442 of the center portion 440 of the stationary housing 426 to their first position, thus forming a locking structure preventing or blocking subsequent insertion of the SULU 418 into the stationary housing 426. That is, the sidewalls 442 are obstructed by the sidewalls of the cartridge receiving half section so they do not have sufficient space to be pivoted or inclined, thus blocking entry of SULU 418 therebetween.

Note that the sidewalls 442 can be formed to normally be in the first position. The sidewalls can alternatively be formed to normally be in the non-blocking position and are moved to the blocking position by engagement with the sidewalls of the cartridge receiving half section. In other alternate embodiments, the sidewalls 442 can be formed such that the sidewalls 442 require manual application of force to pivot between both first and second positions.

As can be appreciated, FIGS. 35-36B illustrate different embodiments of lockout structure that can be used to prevent insertion of the SULU into the stationary housing 326 or 426 if the stationary housing is mounted to the cartridge receiving half-section prior to the insertion of the SULU into the stationary housing. In preferred embodiments, the SULU and respective stationary housing 326, 426 are disposable and the cartridge and anvil receiving sections are reusable.

The SULU and stationary housing 326 or 426 can together be considered the firing assembly (320 and 420 of FIGS. 35 and 36, respectively), with the stationary housing containing the pusher assembly to advance (fire) staples from the SULU.

It will be understood that various modifications may be made to the embodiments of the surgical fastener applying apparatus disclosed herein. Therefore, the above description should not be construed as limiting, but merely as exemplifications of embodiments. Those skilled in the art will envision other modifications within the scope and spirit of the present disclosure.

What is claimed is:

1. A surgical fastener applying apparatus comprising:
an anvil half-section including a distal anvil portion and a proximal handle portion;
a cartridge receiving half-section defining an elongated channel member;
a stationary housing configured to be releasably supported within the elongated channel member of the cartridge receiving half-section, the stationary housing having a proximal portion supporting firing components of the apparatus, a distal portion dimensioned to releasably receive a single use loading unit, and a central portion including a lockout structure, the lockout structure being movable from a first position that prevents full insertion of the single use loading unit into the stationary housing and a second position that allows insertion of the loading unit into the stationary housing, wherein the lockout structure is retained in the first position when the stationary housing is received in the elongated channel member.

2. The surgical fastener applying apparatus according to claim 1, wherein the lockout structure includes a pair of sidewalls and a pair of flanges extending transversely from a top of each sidewall.

3. The surgical fastener applying apparatus according to claim 2, wherein in the first position, the sidewalls are substantially parallel with respect to each other, and the flanges define a first lateral dimension therebetween which is less than a lateral dimension of the single use loading unit.

4. The surgical fastener applying apparatus according to claim 3, wherein in the second position, the sidewalls are inclined away from each other, and the flanges define a second lateral dimension therebetween which is larger than the lateral dimension of the single use loading unit.

5. The surgical fastener applying apparatus according to claim 2, wherein the sidewalls of the central portion are connected to the proximal and distal portions of the stationary housing by living hinges, such that the sidewalls of the central portion are pivotable with respect to the proximal and distal portions.

6. The surgical fastener applying apparatus according to claim 2, wherein the lockout structure includes a bottom surface, and the sidewalls are hingedly attached to the bottom surface.

7. The surgical fastener applying apparatus according to claim 2, wherein the lockout structure is biased to the first position.

8. The surgical fastener applying apparatus according to claim 1, wherein the stationary housing, the firing components, and the single use loading unit form a single disposable unit when the single use loading unit is positioned within the stationary housing.

9. The surgical fastener applying apparatus according to claim 1, wherein the firing components include a knife actuating bar, a cam bar, a guide block and a slide block.

* * * * *